US012753393B2

(12) United States Patent
Nasajpour et al.

(10) Patent No.: US 12,753,393 B2
(45) **Date of Patent: *Oct. 6, 2026**

(54) LIQUID CRYSTAL SCAFFOLDS AND USE THEREOF FOR ORGANOID, SPHEROID, AND 3D CELLAGGREGATE MANUFACTURING

(71) Applicant: THE REGENTS OF THE UNIVERSITY OF CALIFORNIA, Oakland, CA (US)

(72) Inventors: Amir Nasajpour, Los Angeles, CA (US); Paul S. Weiss, Los Angeles, CA (US); Ali Tamayol, Providence, RI (US); Mohamadmahdi Samandari, New Britain, CT (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/246,227

(22) Filed: Jun. 23, 2025

(65) Prior Publication Data

US 2025/0313808 A1 Oct. 9, 2025

Related U.S. Application Data

(63) Continuation-in-part of application No. PCT/US2023/085628, filed on Dec. 22, 2023.

(60) Provisional application No. 63/477,082, filed on Dec. 23, 2022.

(51) Int. Cl.
*C12N 5/09* (2010.01)
*C09K 19/32* (2006.01)
*G01N 33/50* (2006.01)

(52) U.S. Cl.
CPC ............ *C12N 5/0693* (2013.01); *C09K 19/32* (2013.01); *G01N 33/5011* (2013.01); *G01N 33/5082* (2013.01); *C12N 2503/02* (2013.01); *C12N 2509/00* (2013.01); *C12N 2513/00* (2013.01); *C12N 2533/20* (2013.01); *C12N 2539/10* (2013.01)

(58) Field of Classification Search
CPC ............ C12N 2513/00; C12N 2533/20; C12N 2535/10; C12N 2539/00; C12N 2523/00
See application file for complete search history.

(56) References Cited

U.S. PATENT DOCUMENTS

| | | | | |
|---|---|---|---|---|
| 4,514,499 | A * | 4/1985 | Noll | C12M 25/06 435/395 |
| 4,999,348 | A | 3/1991 | Cioca | |
| 7,122,227 | B2 | 10/2006 | Vaughn-Spickers | |
| 10,481,311 | B2 | 11/2019 | Yanai | |
| 10,482,311 | B2 | 11/2019 | Wu | |
| 10,513,691 | B2 | 12/2019 | Matheu | |
| 2007/0237747 | A1 * | 10/2007 | Angel | G01N 33/5005 435/373 |
| 2012/0071618 | A1 | 3/2012 | Goldfinger | |
| 2016/0046761 | A1 | 2/2016 | Hegmann | |
| 2016/0305043 | A1 | 10/2016 | Pham | |
| 2017/0133521 | A1 | 5/2017 | Allen | |
| 2018/0143438 | A1 | 5/2018 | Oh | |
| 2018/0143470 | A1 | 5/2018 | Oh | |
| 2019/0111185 | A1 | 4/2019 | Hegmann | |
| 2026/0062518 | A1 * | 3/2026 | Ware | B29C 48/05 |

FOREIGN PATENT DOCUMENTS

| | | | |
|---|---|---|---|
| CN | 110129259 | 8/2019 | |
| WO | 2008101051 | 8/2008 | |
| WO | 2022020752 | 1/2022 | |
| WO | 2022120120 | 6/2022 | |
| WO | WO-2022115295 A1 * | 6/2022 | C12M 29/14 |

OTHER PUBLICATIONS

Bera et al (Applied Materials and Interfaces, 2015, vol. 7, pp. 14528-14535) (Year: 2015).*
Soon et al (Cytotechnology, 2018, vol. 70, pp. 13-29) (Year: 2018).*
Pandurangang and Kim (Applied Microbiology and Biotechnology, 2015, vol. 99, pp. 5391-5395) (Year: 2015).*
Prevot et al (JOVE, 2017, vol. 122, article e55452, 11 pages) (Year: 2017).*
Sumbal et al (Frontiers in Cel Development and Biology, Mar. 2020, vol. 8, Article 68, 13 pages) (Year: 2020).*
Kim et al (Scientific Reports, 2016, vol. 6, article 35145, 13 pages) (Year: 2016).*
Hanley et al (Molecular Cancer Research, 2020, vol. 18, pp. 1615-1622) (Year: 2020).*
Cai et al (Cells, Apr. 2022, vol. 11, Article 1436, 16 pages) (Year: 2022).*
Rorder et al (Journal of Functional Biomaterials, 2015, vol. 6, pp. 1054-1063) (Year: 2015).*
Ahmad et al., 2018, "Synthesis and characterisation of nickel oxide reinforced with polycaprolactone composite for dielectric applications by controlling nickel oxide as a filler", Results in Physics, 11:427-435.
Andrienko et al., 2018, "Introduction to Liquid Crystals", J. Mol. Liq., 267:520-541.
Babakhanova et al., 2020, "Cell Alignment by Smectic Liquid Crystal Elastomer Coatings with Nanogrooves", J. Biomed. Mater. Res., 108:1223-1230.
CellTracker™ fluorescent probes, 2018, thermofisher.com/document-connect/document-connect.html?url=https%3A%2F%2Fassets.thermofisher.com%2FTFS-Assets%2FLSG%2Fmanuals%2FMAN0001826_CellTracker_Probes_PI.pdf, 4 pages.

(Continued)

*Primary Examiner* — Karen A. Canella
(74) *Attorney, Agent, or Firm* — Riverside Law LLP

(57) ABSTRACT

The present invention provides liquid crystals and compositions thereof (e.g., liquid crystal-based scaffolds) for manufacturing various organoids, such as tumor organoids, as well as spheroids and/or 3D cell aggregates.

19 Claims, 18 Drawing Sheets

(56) References Cited

OTHER PUBLICATIONS

Chlanda et al., 2018, "Structure and Physico-Mechanical Properties of Low Temperature Plasma Treated Electrospun Nanofibrous Scaffolds Examined with Atomic Force Microscopy", Micron, 107:79-84.
Davidson et al., 2019, "Engineered Fibrous Networks to Investigate the Influence of Fiber Mechanics on Myofibroblast Differentiation", ACS Biomater. Sci. Eng., 5:3899-3908.
Dowling et al., 2010, "Effect of Surface Wettability and Topography on the Adhesion of Osteosarcoma Cells on Plasma-Modified Polystyrene", J. Biomater. Appl., 26:327-347.
Dyro et al., 1975, "Dynamic Viscoelastic Properties of Cholesteric Liquid Crystals", Mol. Cryst. Liq. Cryst., 29:263-284.
Elser et al., 1976, "Selective Reflection of Cholesteric Liquid Crystals", Advances in Liquid Crystals, 2:73-172.
Enz et al., 2013, "Confinement-Sensitive Optical Response of Cholesteric Liquid Crystals in Electrospun Fibers", ACS Nano, 7:6627-6635.
Ferrantini et al., 2019, "Development of Light-Responsive Liquid Crystalline Elastomers to Assist Cardiac Contraction", Circ. Res., 124:e44-e54, 11 pages.
Gao et al., 2016, "Biocompatible 3D Liquid Crystal Elastomer Cell Scaffolds and Foams with Primary and Secondary Porous Architecture", ACS Macro Lett., 5:4-9.
Ghosh et al., 2007, "Cell Adaptation to a Physiologically Relevant ECM Mimic with Different Viscoelastic Properties", Biomaterials, 28:671-679.
Hwang et al., 2002, "Self-Assembling Biomaterials: Liquid Crystal Phases of Cholesteryl oligo(L-lactic acid) and Their Interactions with Cells", Proc. Natl. Acad. Sci. USA, 99:9662-9667.
Jewell et al., 2011, "Living Systems and Liquid Crystals", Liq. Cryst., 38:1699-1714.
Krigbaum et al., 1983, "Thermotropic Polyesters. 2. Investigation of the Mesophase Properties of Polymers Based on 4,4'-Dihydroxybiphenyl. Macromolecules", Macromolecules, 16:1271-1279.
Liu D et al., 2014, "Self-Assembled Dynamic 3D Fingerprints in Liquid-Crystal Coatings Towards Controllable Friction and Adhesion", Angew. Chem. Int. Ed., 53:4542-4546.
Martella et al., 2018, "Advances in Cell Scaffolds for Tissue Engineering: The Value of Liquid Crystalline Elastomers", Chem. Eur. J., 24:12206-12220.
Martella et al., 2019, "Liquid Crystal-Induced Myoblast Alignment", Adv. Healthc. Mater., 8:1801489, 28 pages.
Maxfield et al., 2005, "Role of Cholesterol and Lipid Organization in Disease", Nature, 438:612-621.
Mensah et al., 2020, "Complex permittivity and power loss characteristics of α-Fe2O3/polycaprolactone (PCL) nanocomposites: effect of recycled α-Fe2O3 nanofiller", Heliyon, 6:e05595, 7 pages.
Mitov et al., 2017, "Cholesteric Liquid Crystals in Living Matter", Soft Matter, 13:4176-4209.
Mohamed et al., 2019, "Stimuli-Responsive Hydrogels for Manipulation of Cell Microenvironment: From Chemistry to Biofabrication Technology", Prog. Polym. Sci., 98:101147, 78 pages.
Mori et al., 2020, "3D Porous Liquid Crystal Elastomer Foams Supporting Long-term Neuronal Cultures", Macromolecular Rapid Communications, 41:1900585, 5 pages.
Nasajpour A et al., 2017, "Nanostructured Fibrous Membranes with Rose Spike-Like Architecture", Nano Lett., 17:6235-6240.
Nasajpour et al., 2018, "A Multifunctional Polymeric Periodontal Membrane with Osteogenic and Antibacterial Characteristics", Adv. Funct. Mater., 28:1703437, 8 pages.
Nasajpour et al., 2020, "Cholesteryl Ester Liquid Crystal Nanofibers for Tissue Engineering Applications", ACS Mater. Lett., 2020, 2:1067-1073.
Nguyen et al., 2020, "Thermochromic Fibers via Electrospinning", Polymers, 12:842, 15 pages.
Ostuni et al., 2001, "Self-Assembled Monolayers That Resist the Adsorption of Proteins and the Adhesion of Bacterial and Mammalian Cells", Langmuir, 17:6336-6343.
Patteson et al., 2018, "The Propagation of Active-Passive Interfaces in Bacterial Swarms", Nat. Commun., 9:5373, 10 pages.
Pérez-González et al., 2019, "Active Wetting of Epithelial Tissues", Nat. Phys., 15:79-88.
Prevot et al., 2017, "From Biomaterial, Biomimetic, and Polymer to Biodegradable and Biocompatible Liquid Crystal Elastomer Cell Scaffolds", Advances in Bioinspired and Biomedical Materials vol. 2 ACS Symposium Series; American Chemical Society: Washington, DC, 2017, 43 pages.
Prevot et al., 2017, "New developments in 3D liquid crystal elastomers scaffolds for tissue engineering: from physical template to responsive substrate", Proceedings of SPIE, 10361:103610T, 11 pages.
Prevot et al., 2018, "Liquid crystal elastomer foams with elastic properties specifically engineered as biodegradable brain tissue scaffolds", Soft Matter, 14:354-360.
Prevot et al., 2018, "Liquid Crystal Elastomers—A Path to Biocompatible and Biodegradable 3D-LCE Scaffolds for Tissue Regeneration", Materials, 11:377, 21 pages.
Samandari et al., 2017, "Ultrasound Induced Strain Cytoskeleton Rearrangement: An Experimental and Simulation Study", J. Biomech., 60:39-47.
Saw TB et al., 2017, "Topological Defects in Epithelia Govern Cell Death and Extrusion", Nature, 544:212-216.
Sharma et al., 2014, "Biocompatible, Biodegradable and Porous Liquid Crystal Elastomer Scaffolds for Spatial Cell Cultures: Biocompatible, Biodegradable and Porous LC Elastomers", Macromolecular Bioscience, 15:200-214.
Shen et al., 2011, "Viscoelastic Properties of Isolated Collagen Fibrils", Biophys. J., 100:3008-3015.
Shi et al., 2010, "Do Electrospun Polymer Fibers Stick?", Langmuir, 26:14188-14193.
Sleep et al., 2017, "Injectable Biomimetic Liquid Crystalline Scaffolds Enhance Muscle Stem Cell Transplantation", Proc. Natl. Acad. Sci. USA, 114:E7919-E7928, 10 pages.
Soon et al., 2011, "Influence of Time Dependent Factors to the Phases and Poisson's ratio of Cholesteryl Ester liquid crystals", J. Science and Technology, 13:-20 pages.
Soon et al., 2014, "Biophysical characteristics of cells cultured on cholesteryl ester liquid crystals", Micron, 56:73-79.
Suhasini et al., 2018, "Synthesis, thermal and magnetic behavior of iron oxide-polymer nanocomposites", Sci Eng Compos Mater, 25:189-195.
Sung et al., 2018, "Liquid-crystalline nanoarchitectures for tissue engineering", Beilstein J. Nanotechnol., 9:205-215.
Tibbitt et al., 2017, " Living Biomaterials", Acc. Chem. Res., 50:508-513.
Turiv et al., 2020, "Topology Control of Human Fibroblast Cells Monolayer by Liquid Crystal Elastomer", Sci. Adv., 6: eaaz6485, 10 pages.
Van der Werff et al., 2012, "Combinatorial Approach for the Rapid Determination of Thermochromic Behavior of Binary and Ternary Cholesteric Liquid Crystalline Mixtures", ACS Comb. Sci., 14:605-612.
Van Hecke et al., 2005, "Synthesis and Physical Properties of Liquid Crystals: An Interdisciplinary Experiment", J. Chem. Educ., 82:1349-1354.
Xie et al., 2020, "Construction and Biocompatibility of Three-Dimensional Composite Polyurethane Scaffolds in Liquid Crystal State", ACS Biomater. Sci. Eng., 6:2312-2322.
Xu et al., 2007, "On the Modified Tabor Parameter for the JKR-DMT Transition in the Presence of a Liquid Meniscus", J. Colloid Interface Sci., 315:772-785.
Young et al., 2016, "Nanoscale and Mechanical Properties of the Physiological Cell—ECM Microenvironment", Exp. Cell Res., 343:3-6.

* cited by examiner

PDMS

CLC

LIQUID CRYSTAL SCAFFOLDS AND USE THEREOF FOR ORGANOID, SPHEROID, AND 3D CELLAGGREGATE MANUFACTURING

CROSS-REFERENCE TO RELATED APPLICATIONS

This application is a Continuation-In-Part application claiming priority to the PCT International Patent Application PCT/US2023/085628, filed Dec. 22, 2023, claiming priority to U.S. Provisional Patent Application No. 63/477,082, filed Dec. 23, 2022, the disclosures of which are hereby incorporated by reference herein in their entireties.

BACKGROUND OF THE INVENTION

The liquid crystalline (LC) phase shares properties seen in both liquids and solids. Historically, LC-based materials have been applied in commercial applications with great success, such as in the development of body armor KEVLAR® and the fabrication of modern liquid crystal displays (Andrienko D et al., 2018, J. Mol. Liq., 267:520-541). More recently, LCs have been used to mimic various biological processes, ranging from epithelial tissue organization, bacterial biofilm formation, and the assembly of many biologically derived materials (Saw T B et al., 2017, Nature, 544:212-216; Pérez-González C et al., 2019, Nat. Phys., 15:79-88; Patteson A E et al., 2018, Nat. Commun., 9:5373; Mitov M et al., 2017, Soft Matter, 13:4176-4209; Jewell S A et al., 2011, Liq. Cryst., 38:1699-1714). The synthesis of LC biomaterials is poised to address challenges in recapitulating mechanics seen in the native extracellular matrix (ECM) (Tibbitt M W et al., 2017, Acc. Chem. Res., 50:508-513; Martella D et al., 2018, Chem.: Eur. J., 24:12206-12220; Mohamed M A et al., 2019, Prog. Polym. Sci., 98:101147). An associated challenge for engineering LCs into tissue engineering substrates is the cytotoxicity associated with most commercially available LC mesogens.

Thus, there is a need in the art for methods and technologies that produce liquid-crystal-based biomaterials for the development of dynamic and responsive interfaces for tissue engineering, such as organoid, spheroid, and 3D cell aggregate manufacturing. The present invention satisfies this unmet need.

SUMMARY OF THE INVENTION

In another aspect, the present invention relates to a method of manufacturing a 3D cell aggregate. In some embodiments, the method comprises culturing at least one anchorage-dependent cell in the presence of a liquid crystal or a composition thereof.

In some embodiments, the 3D cell aggregate comprises at least one selected from the group consisting of a spheroid, a tumor spheroid, a stem cell spheroid, an organoid, a tumor organoid, a meat organoid, a fish organoid, an insulin generating organoid, a milk generating organoid, a blood generating organoid, a blood cell organoid, a blood product generating organoid, an extracellular matrix organoid, a stem cell organoid, and a mixture of cells and biomaterials, polymers, lipids, phospholipids, proteins, or drugs.

In some embodiments, the method comprises culturing the at least one anchorage-dependent cell in the liquid crystal or composition thereof, on a surface of the liquid crystal or composition thereof, or both.

In some embodiments, the at least one anchorage-dependent cell is at least one selected from the group consisting of a cancer cell, an epithelial cell, an endothelial cell, a fibroblast, a muscle cell, a myoblast cell, a neuron, an adipocyte, a cardiac cell, a hematopoietic a stem cell, a bone marrow cell, a gland cell, a mammary gland cell, a human mammary gland cell, an epidermal cell, a keratinocyte, a lactocytes, a hepatic cell, a beta cells pancreatic cell, a human cell, a mammalian cell, a vertebrate cell, an invertebrate cell, a bacterial cell, a human dermal fibroblast, a human keratinocyte, a human epidermal cell, a human cancer cell, a human brain cancer cell, a bovine satellite cell, a C2C12 myoblast, an induced pluripotent stem cell (iPSC), a mesenchymal stem cell (MSC), and an iPSC muscle progenitor.

In some embodiments, the liquid crystal or composition thereof comprises at least one selected from the group consisting of cholesteryl oleyl carbonate or a derivative thereof, cholesteryl pelargonate or a derivative thereof, and cholesteryl benzoate or a derivative thereof.

In some embodiments, the liquid crystal is a cholesteryl ester liquid crystal.

In some embodiments, the liquid crystal or composition thereof displays a phase change between about 32° C. and about 42° C.

In some embodiments, the liquid crystal or composition thereof comprises a pattern that controls cellular organization, affects the shape of the cell cultures, or both.

In some embodiments, the composition comprises at least one selected from the group consisting of a composite, a substrate, and an additive. In some embodiments, the composition comprises at least one component selected from the group consisting of a composite, a substrate, a cholesteryl ester liquid crystal-based scaffold, and an additive, wherein the at least one component is not covalently bound to the liquid crystal.

In some embodiments, the method comprises the steps of inducing a phase change of the liquid crystal or composition thereof and inducing cellular aggregation of the at least one anchorage-dependent cell.

In some embodiments, the method further comprises the steps of dissociating the liquid crystal and detaching the cultured cells. In some embodiments, the step of detaching the cultured cells comprises at least one of enzymatic treatment, mechanical force, fluid shear force, acoustic waves, self-migration of the cells by tilting, and self-migration of the cells by chemical signals.

In some embodiments, the method further comprises the step of coating a surface of a substrate with the liquid crystal or composition thereof.

In some embodiments, the substrate is a multi-well plate for multiplexed bioassays.

In another aspect, the present invention relates to a method of co-culturing at least one anchorage-dependent cell with at least one second cell, wherein the method comprises co-culturing the cells in the presence of a liquid crystal or a composition thereof.

In some embodiments, the method comprises at least one of controlling organization, ordering addition of the cells, and cell-directing organization of the cells.

In another aspect, the present invention relates to a method of evaluating a cancer treatment. In some embodiments, the method comprises manufacturing at least one 3D cell aggregate using the method of the present invention; applying the cancer treatment to the 3D cell aggregate; measuring a variable of the 3D cell aggregate; and determining the cancer treatment is effective when the variable of the 3D cell aggregate decreased when compared to a comparator.

In some embodiments, the variable of the 3D cell aggregate comprises at least one selected from the group consisting of a size of the 3D cell aggregate, viability of the 3D cell aggregate, metabolic activity of the 3D cell aggregate, cellular behavior of the 3D cell aggregate, proteomics of the 3D cell aggregate, lipidomics of the 3D cell aggregate, and transcriptomics of the 3D cell aggregate.

In another aspect, the present invention relates to a method of manufacturing an organoid. In some embodiments, the organoid is selected from a tumor organoid, meat organoid, fish organoid, insulin generating organoid, milk generating organoid, blood generating organoid, blood cell organoid, blood product generating organoid, extracellular matrix organoid, stem cell organoid, or any combination thereof. In some embodiments, the organoid is a mixture of cells and biomaterials, polymers, lipids, phospholipids, proteins, drugs, and/or nanomaterials to add functionality to organoids.

In another aspect, the present invention relates to a method of manufacturing a spheroid. In some embodiments, the spheroid is selected from a tumor spheroid, stem cell spheroid, or any combination thereof.

In another aspect, the present invention relates to a method of manufacturing a 3D cell aggregate.

In another aspect, the present invention relates to a method of co-culturing at least one cell with at least one second cell.

In some embodiments, the cells are co-cultured at the same time to make a cell-directed organization of the cells.

In some embodiments, the method comprises ordered addition of the cells.

In some embodiments, the method comprises controlled organization. In one embodiment, the organization is a core-shell organization. In some embodiments, the cells are co-cultured to form a core-shell organization.

In various embodiments, the method comprises culturing at least one cell in the presence of a liquid crystal or a composition thereof. In some embodiments, the method comprises culturing at least one cell in a liquid crystal or a composition thereof. In some embodiments, the method comprises culturing at least one cell on a surface of a liquid crystal or a composition thereof. In some embodiments, the method comprises culturing at least one cell on a surface of a liquid crystal or a composition thereof to form a 3D cell culture.

In some embodiments, the cell is selected from a cancer cell, epithelial cell, endothelial cell, fibroblast, muscle cell, myoblast cell, neuron, adipocyte, cardiac cell, hematopoietic stem cell, bone marrow cell, gland cell, mammary gland cell, human mammary gland cell, epidermal cell, keratinocyte, bovine satellite cell, or any combination thereof.

In some embodiments, the cell is selected from a human cell, mammalian cell, vertebrate cell, invertebrate cell, bacterial cell, or any combination thereof.

In some embodiments, the cell is selected from a human dermal fibroblast, human keratinocyte, human epidermal cell, cancer cell, human cancer cell, human brain cancer cell, cardiac cell, bovine satellite cell, C2C12 myoblast, iPSC, MSC, iPSC muscle progenitor, or any combination thereof.

In some embodiments, the method comprises culturing the at least one cell on a surface of the liquid crystal or the composition thereof.

In some embodiments, the liquid crystal comprises a pattern. In some embodiments, the pattern comprises a 2D patterning, 3D patterning, or a combination thereof. In one embodiment, the pattern controls cellular organization. In one embodiment, the pattern affects the shape of the cell cultures.

In some embodiments, the liquid crystal comprises at least one component having a chemical functional group recognized by cells. In some embodiments, this property leads to cellular adhesion and circumvents requirements of other scaffolds that require additives for this purpose.

In some embodiments, the liquid crystal comprises at least one selected from cholesteryl oleyl carbonate, cholesteryl pelargonate, cholesteryl benzoate, or cellulose. In some embodiments, the liquid crystal is a cholesteryl ester liquid crystal. In some embodiments, the liquid crystal is a cellulose-based liquid crystal.

In some embodiments, the composition further comprises at least one selected from a polymer, solvent, composite, substrate, additive, or protein.

In some embodiments, the polymer is selected from an edible polymer, food grade polymer, biocompatible polymer, biodegradable polymer, plant-based polymer, animal-derived polymer, human-derived polymer, or any combination thereof. In some embodiments, the polymer is selected from polyester, polycaprolactone, polyethylene glycol, polysaccharide, alginate, agar, or any combination thereof. In some embodiments, the protein is selected from a zein, soybean protein, vegetable-based protein, prolamin protein, or any combination thereof.

In some embodiments, the composition is a cholesteryl ester liquid crystal-based scaffold.

In some embodiments, the composition is a cellulose-based liquid crystal-based scaffold.

In some embodiments, the liquid crystal serves to move the cells in a place of external stimulus. In some embodiments, the liquid crystal serves to move the cell or cells, in place of external stimulation typically needed by other scaffolds. In some embodiments, the external stimulus comprises a set temperature of an incubator, bioreactor, or vessel growing organoids. In some embodiments, it is the liquid crystalline phase transition that leads to a motion. In some embodiments, the liquid crystal phase transition is set by the choice of components to be near the set temperature or set temperatures of the incubator, bioreactor, or other vessel in which the organoids are grown.

In some embodiments, the liquid crystal or the composition thereof is active at different temperatures.

In some embodiments, the culturing of the at least one cell is performed at different temperatures.

In some embodiments, the culturing of the at least one cell is performed at between about 15° C. and about 40° C. In some embodiments, the culturing of the at least one cell is performed at between about 20° C. and about 40° C. In some embodiments, the culturing of the at least one cell is performed at between about 32° C. and about 40° C. In some embodiments, the culturing of the at least one cell is performed at between about 34° C. and about 38° C. In some embodiments, the culturing of the at least one cell is performed at between about 15° C. and about 23° C. In some embodiments, the culturing of the at least one cell is performed at between about 15° C. and about 20° C. (e.g., for fish cells or invertebrate cells). In some embodiments, the culturing of the at least one cell is performed at between about 23° C. and about 25° C. In some embodiments, the culturing of the at least one cell is performed at between about 27° C. and about 29° C. In some embodiments, the culturing of the at least one cell is performed at between about 30° C. and about 32° C.

In some embodiments, the culturing of the at least one cell is performed for at least 1 hr. In some embodiments, the culturing of the at least one cell is performed for at least 6 hr. In some embodiments, the culturing of the at least one cell is performed for at least 12 hr. In some embodiments, the culturing of the at least one cell is performed for at least 14 hr. In some embodiments, the culturing of the at least one cell is performed for at least 72 hr. In some embodiments, the culturing of the at least one cell is performed for at least 2 weeks (e.g., for muscle differentiation). In some embodiments, the culturing of the at least one cell is performed indefinitely (e.g., for cancer cell growth). In some embodiments, the culturing of the at least one cell is performed until cell culture media and nutrients are removed from cultured environments.

In some embodiments, the cells are cultured on a surface of the liquid crystal in an environment containing biomaterials, lipids, phospholipids, proteins, drugs, nanomaterials, or any combination thereof to add functionality and adjust mechanical properties.

In one aspect, the present invention also provides a method of harvesting cultured cells. In some embodiments, the method comprises a) dissociating the liquid crystal; and b) detaching the cultured cells. In some embodiments, the method comprises detaching the cultured cells by enzymatic treatment, mechanical force, fluid shear force, acoustic waves, self-migration of the cells by tilting, self-migration of the cells by chemical signals, or any combination thereof.

In one aspect, the present invention also provides a method of evaluating a cancer treatment, wherein the method comprises a) manufacturing at least one tumor organoid using the method of the present invention; b) applying the cancer treatment to the tumor organoid; c) measuring a variable of the tumor organoid; and d) determining the cancer treatment is effective when the variable of the tumor organoid decreased when compared to a comparator.

In some embodiments, the variable of the tumor organoids comprises at least one selected from a size of the tumor organoid, viability of the tumor organoid, metabolic activity of the tumor organoid, cellular behavior of the tumor organoid, proteomics of the tumor organoid, lipidomics of the tumor organoid, or transcriptomics of the tumor organoid.

In another aspect, the present invention provides a method of evaluating a cancer treatment, wherein the method comprises a) manufacturing at least one tumor spheroid using the method of the present invention; b) applying the cancer treatment to the tumor spheroid; c) measuring a variable of the tumor spheroid; and d) determining the cancer treatment is effective when the variable of the tumor spheroid decreased when compared to a comparator.

In some embodiments, the variable of the tumor spheroid comprises at least one selected from a size of the tumor spheroid, viability of the tumor spheroid, metabolic activity of the tumor spheroid, cellular behavior of the tumor spheroid, proteomics of the tumor spheroid, lipidomics of the tumor spheroid, or transcriptomics of the tumor spheroid.

In some embodiments, the cancer treatment is tested against tumor organoids.

In some embodiments, the cancer treatment is assessed against organoids prepared from a single patient's tumor cells. In some embodiments, a single patient's tumor cells are co-cultured with other cells to recapitulate the tumor microenvironment for testing the effectiveness of the cancer treatments.

In some embodiments, the cancer treatment is tested against various tumor organoids, to assess the efficacy of the treatments or combinations.

In one aspect, the present invention also provides a method of coating a surface of a substrate, wherein the method comprises coating the surface of the substrate with an organoid or spheroid. In some embodiments, the organoid or spheroid self-assemble into aggregates. In some embodiments, the organoid is manufactured using the method of the present invention. In some embodiments, the spheroid is manufactured using the method of the present invention.

In some embodiments, the surface of the substrate is a slanted surface. In some embodiments, the surface of the substrate is a flat surface for a period of time followed by tilting of the surface for harvesting of the cells.

In some embodiments, the substrate is a multi-well plate for multiplex bioassays.

In some embodiments, the method comprises continuous organoid formation or spheroid formation.

In another aspect, the present invention provides a method of manufacturing an organoid, wherein the method comprises culturing stem cells in the presence of a liquid crystal or a composition thereof. In some embodiments, the method comprises evaluating the development of the stem cells toward different lineages.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 4A and FIG. 4B, depicts representative patterning CLC on the surfaces to control the distribution of C2C12 organoids in culture environment. FIG. 4A depicts representative linear patterns with different width. FIG. 4B depicts representative circular pattern used in future experiments. High patternability was achieved using CLC material.

FIG. 9A and FIG. 9B, depicts representative results demonstrating co-culture of various cell types (C2C12 myoblasts and NIH 3T3 fibroblasts) for formation of multicellular organoids. FIG. 9A depicts representative results demonstrating co-seeding. Different cells were mixer together and seeded on top of the CLC layer. FIG. 9B depicts representative results demonstrating sequential seeding. One cell type was seeded and after 15 h, when organoids were formed, the other cells were added to the culture medium. Mixed and organized organoids were optionally formed by co-culture of various cell types on the CLC coating.

FIG. 13 depicts representative results demonstrating that without the correct ratios, the helix does not form to stimulate organoid assembly.

DETAILED DESCRIPTION

Figure 1:
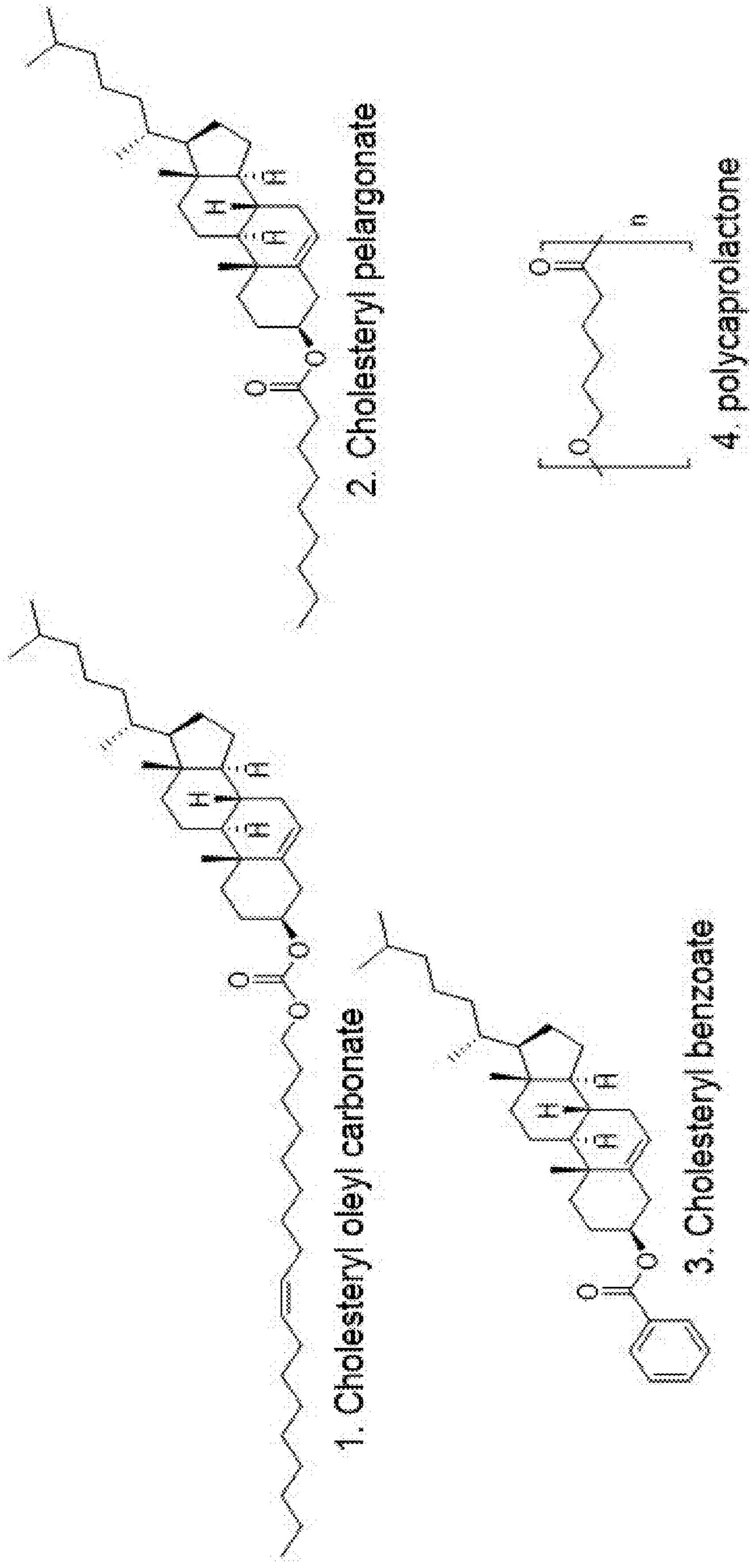
FIG. 1 depicts a schematic representation of chemical structures of the compounds used for the synthesis of the cholesteryl ester liquid crystal scaffolds.
Figure 2:
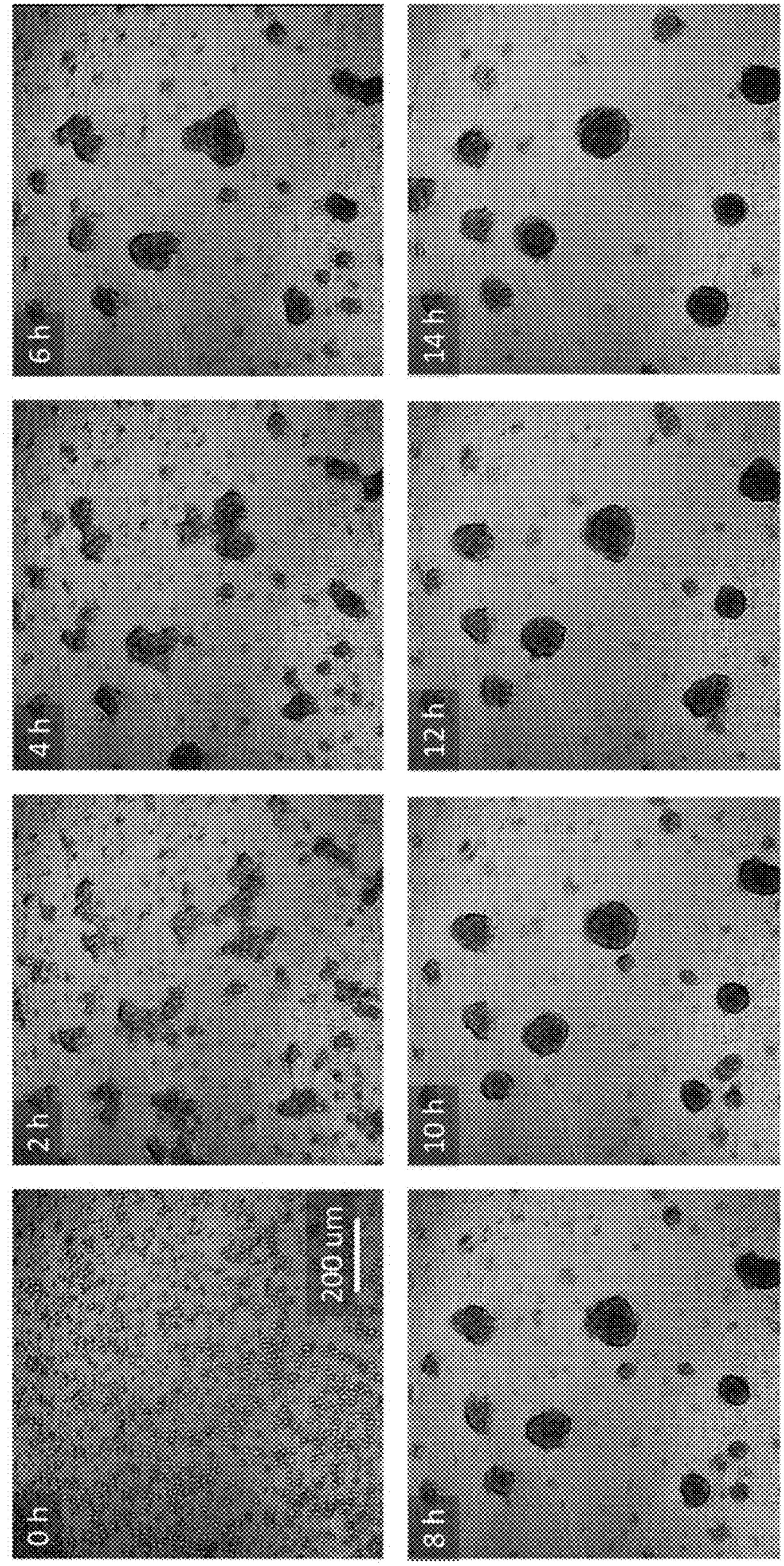
FIG. 2 depicts representative images demonstrating the formation of muscle progenitor organoids over 14 hr.
Figure 3:
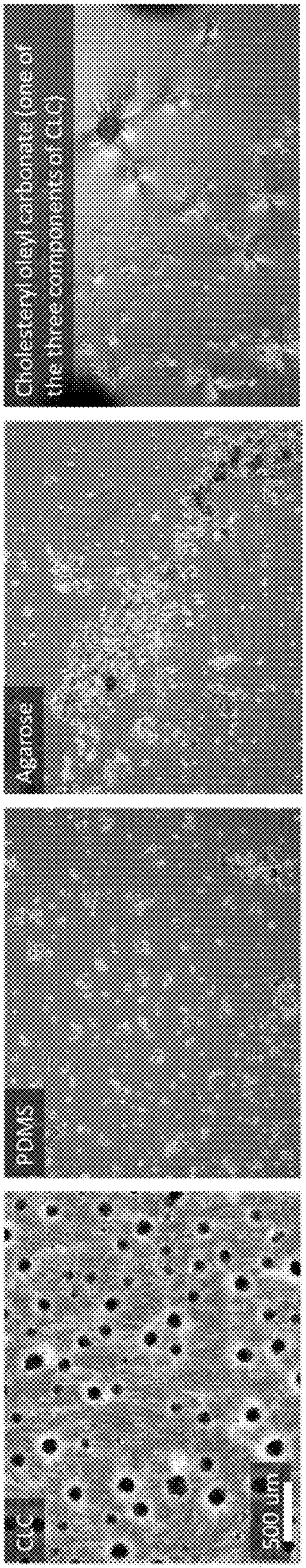
FIG. 3 depicts representative images evaluating the behavior of the myoblasts on CLC compared to materials previously used for organoid formation. Only CLC were able to form organoids in 15 hr post cell seeding.
Figure 4:
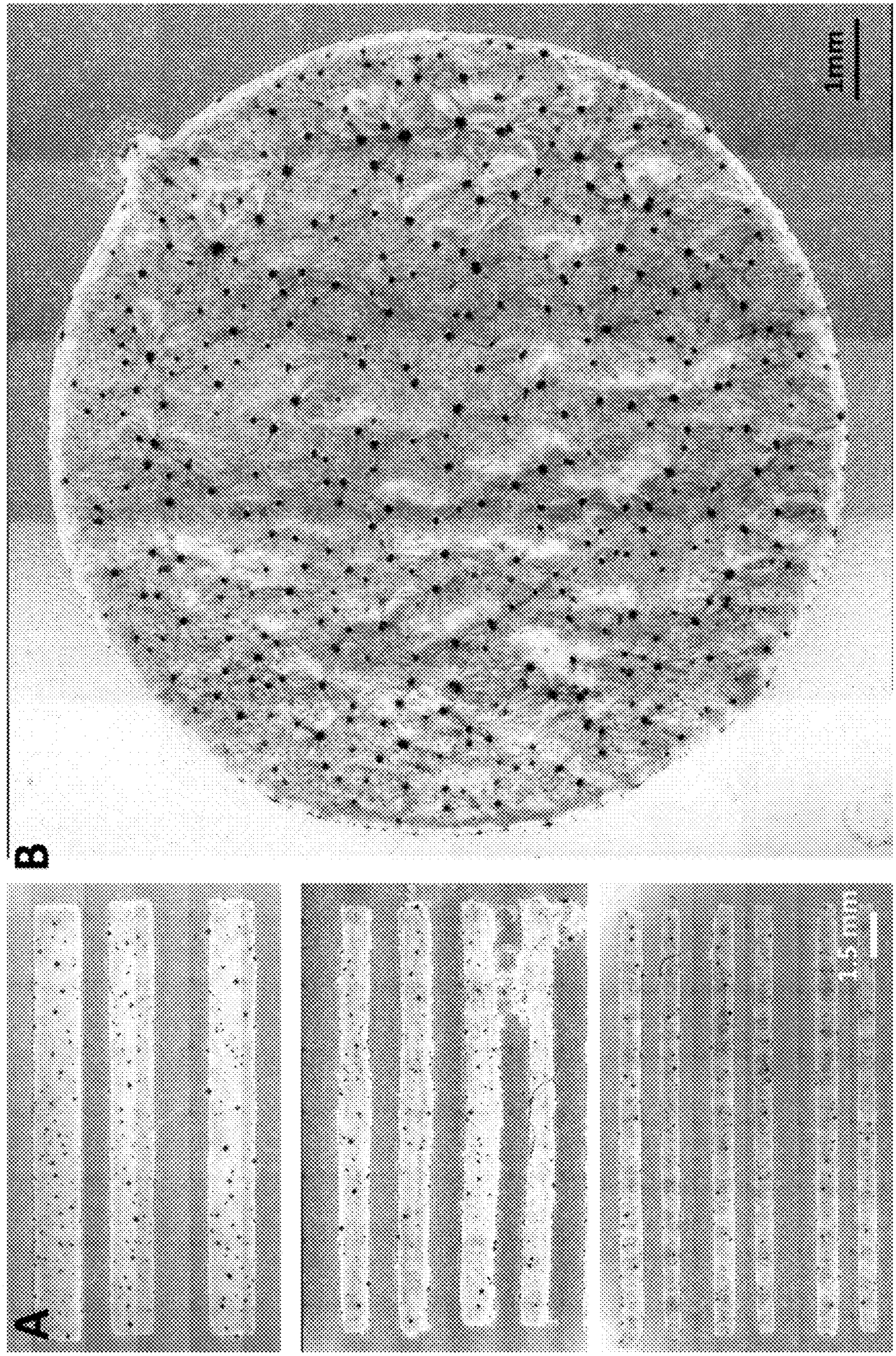
FIG. 4, comprising
Figure 5:
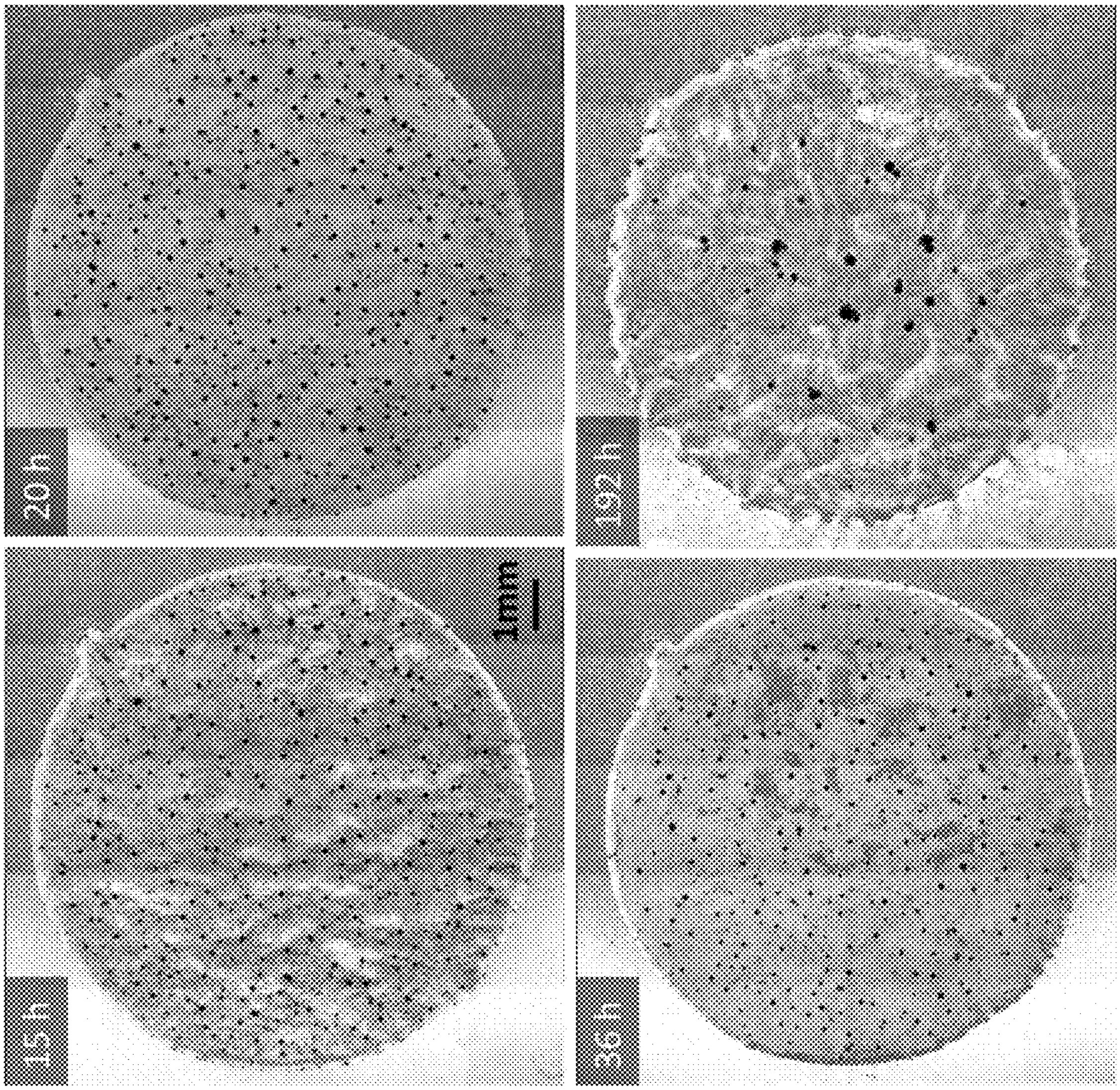
FIG. 5 depicts representative results demonstrating stability of the circular patterns and behavior of the C2C12 cells on the CLC over 8 days of culture. The material and cellular structure demonstrated high stability over multiple days.
Figure 6:
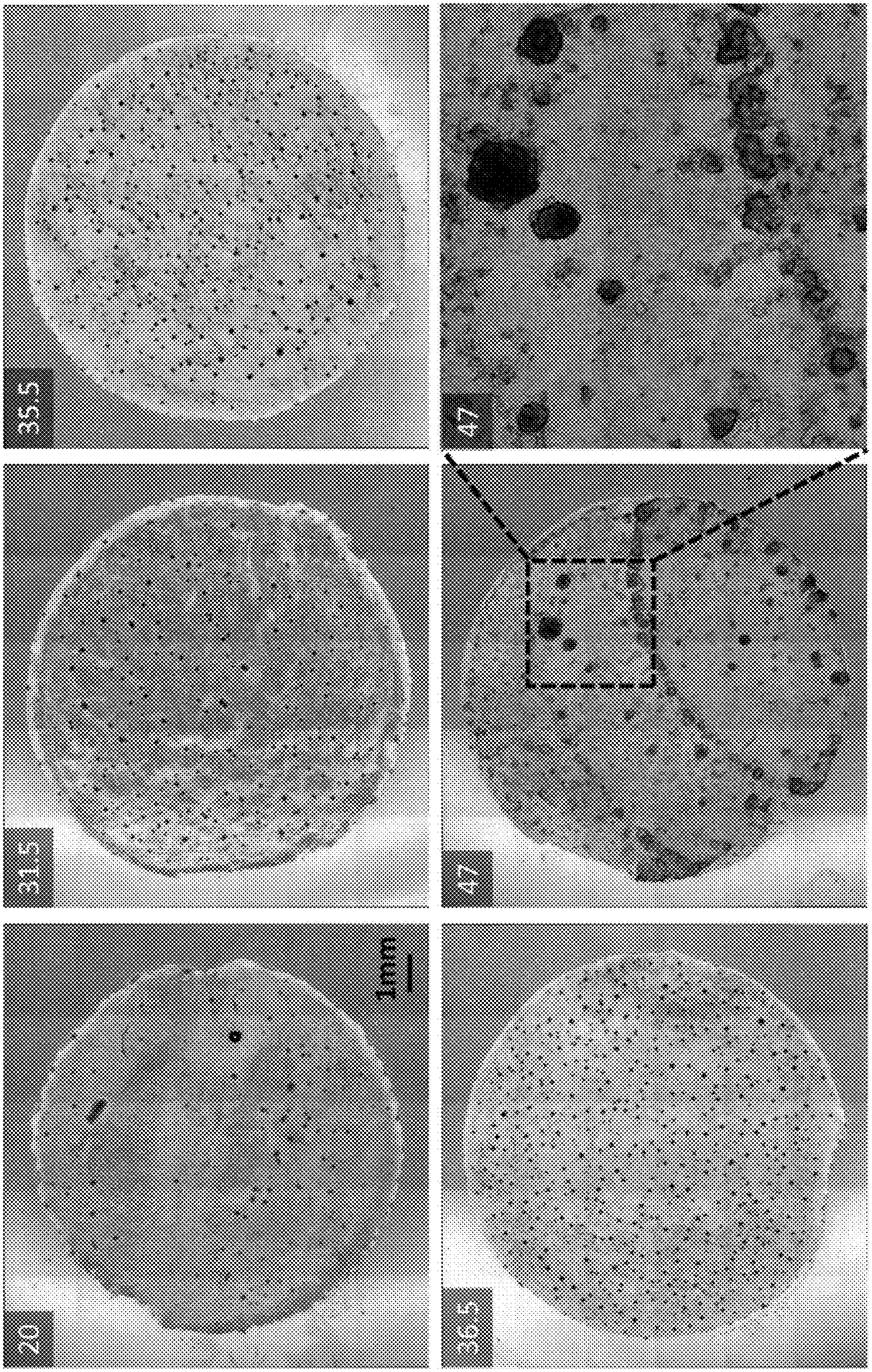
FIG. 6 depicts representative images evaluating the behavior of myoblasts on CLC with different formulations having different transition temperature. The number on the top-left of each panel shows the transition temperature in degrees Celsius. The closer the transition temperature to the incubation temperature, the higher consistency and homogeneity in the organoid formation was seen. In high transition temperatures (47° C. here), the material crystalized at physiological temperature (37° C.) over time. Therefore, identifying cells was not feasible with phase contrast images. Here, a nuclear live staining (blue) was used to label cells. As shown, most of the spots on the material were crystals rather than organoids.
Figure 7:
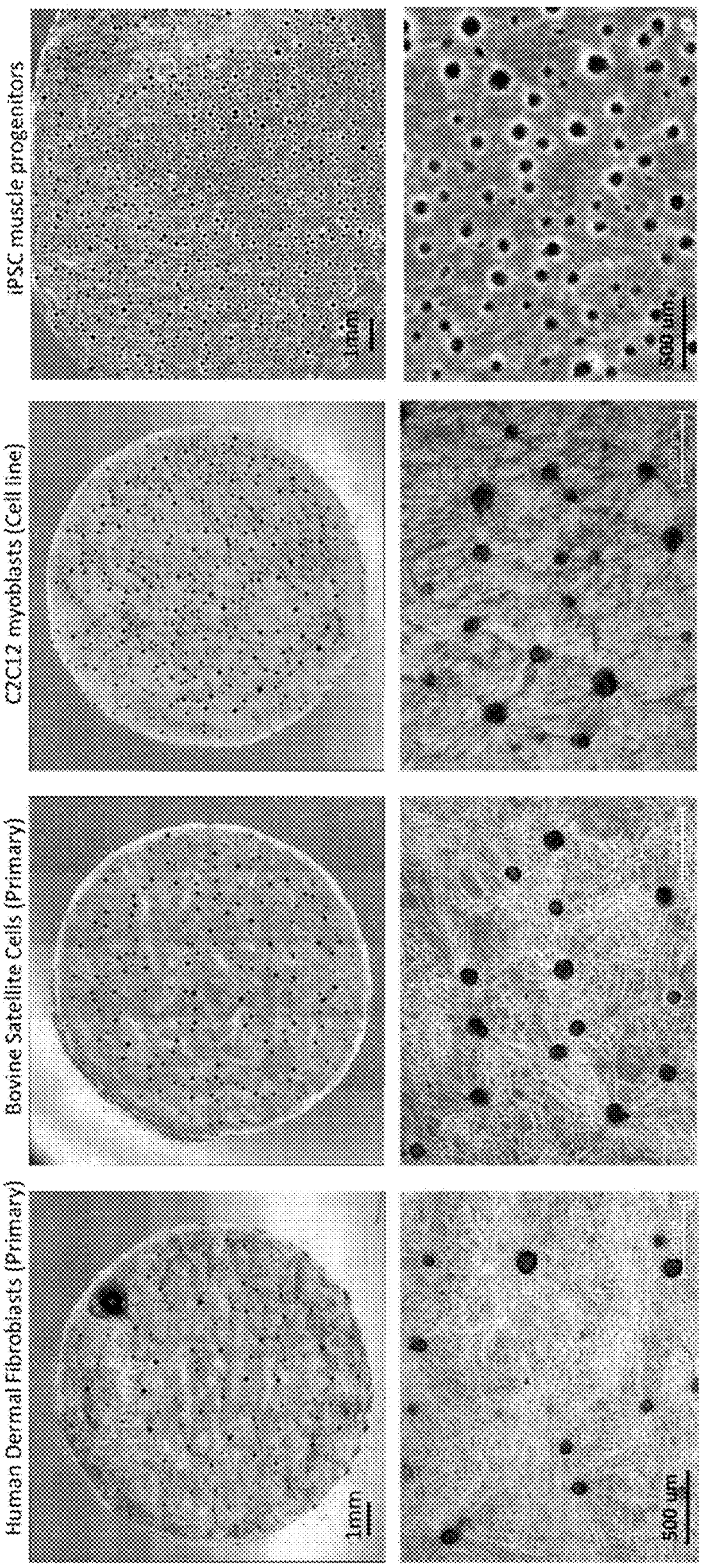
FIG. 7 depicts representative ability of the CLC material to form organoids from various cell types after 15 hr of culture.
Figure 8:
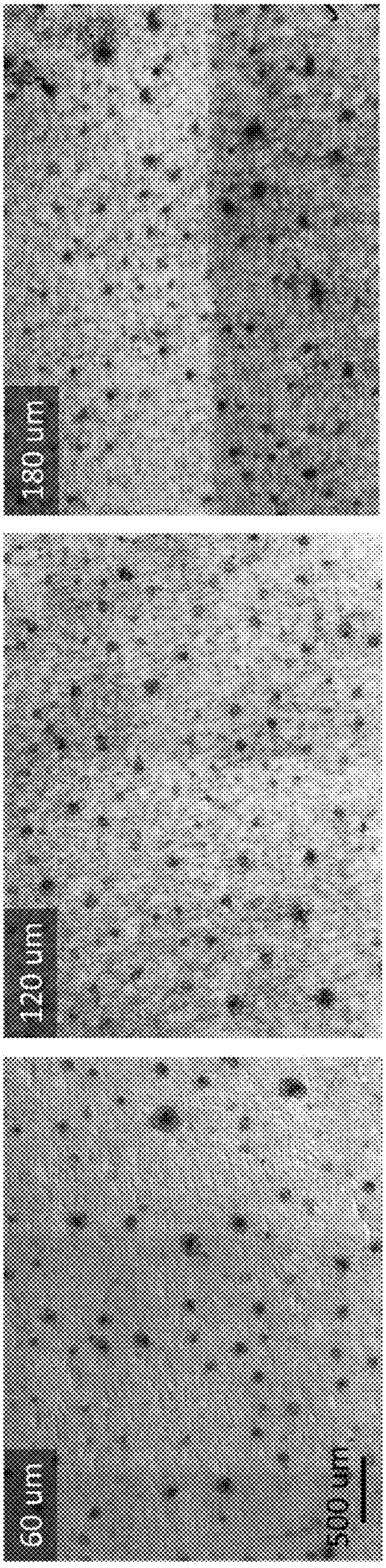
FIG. 8 depicts representative images evaluating the effect of CLC coating on the efficacy of organoid formation. While imaging through thicker layers of CLC was more challenging, the material maintained its capability for formation of organoids after 15 h.
Figure 9:
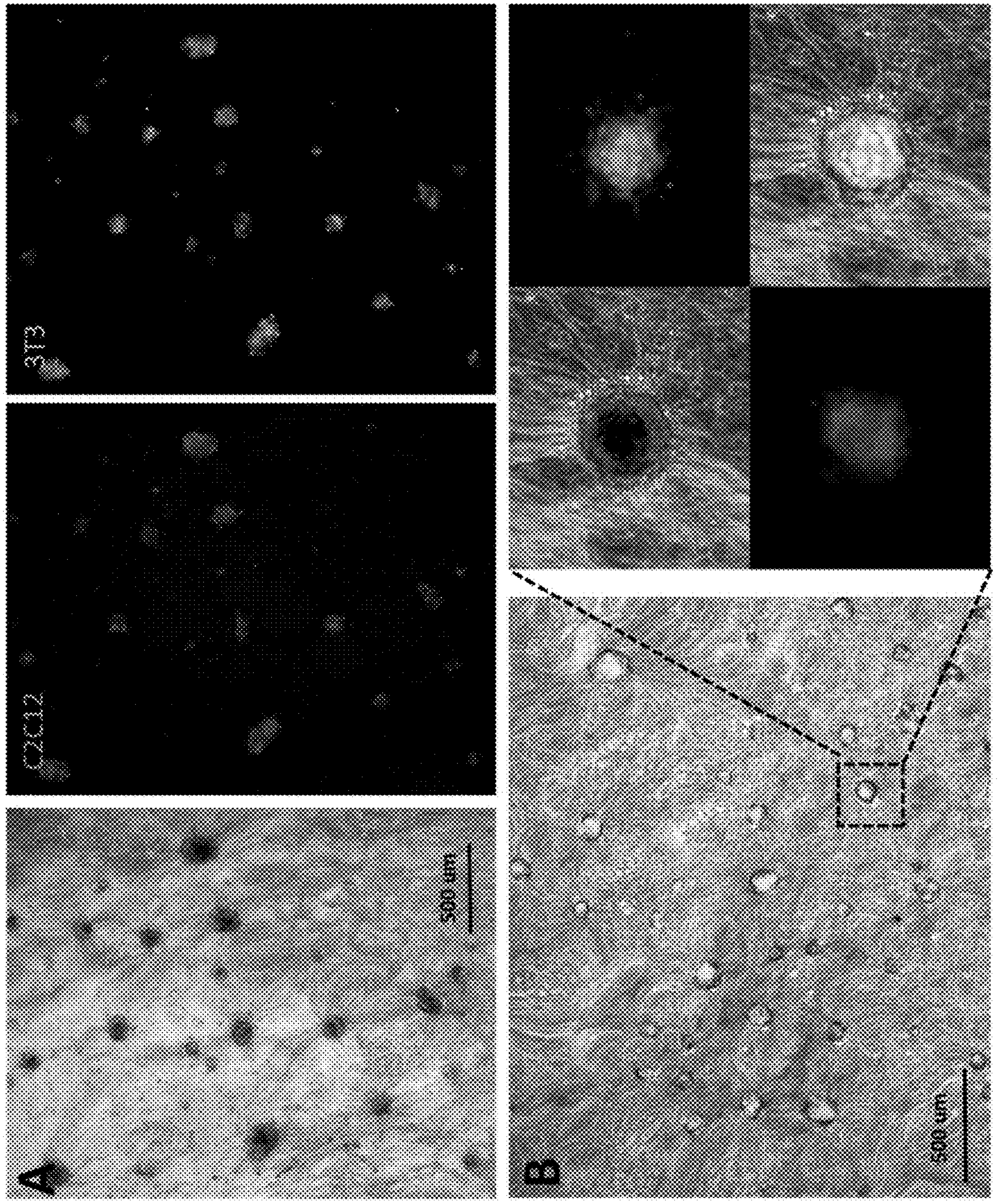
FIG. 9, comprising
Figure 10:
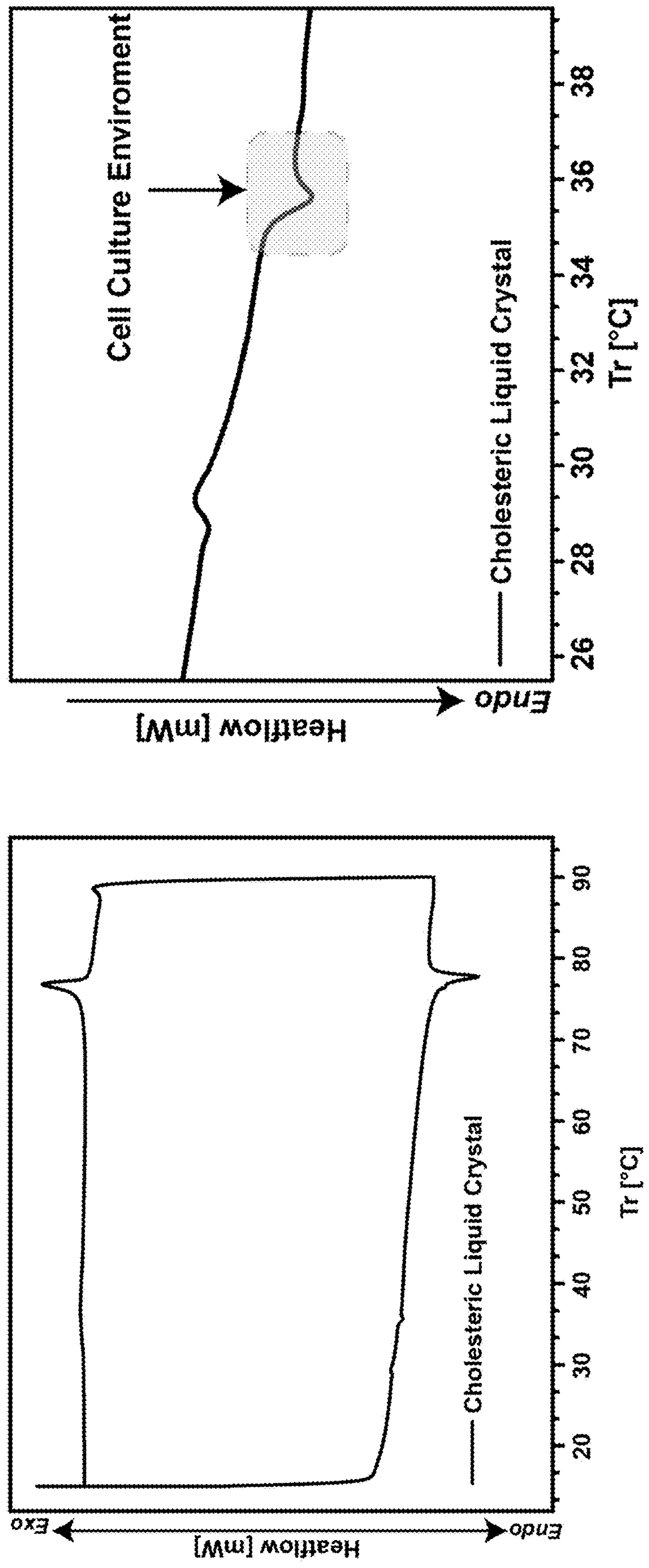
FIG. 10 depicts representative differential scanning calorimeter results indicating cell culture environment of CLC. The experiment depicts a CLC phase transition occurring at cell culture temperature environment.
Figure 11:
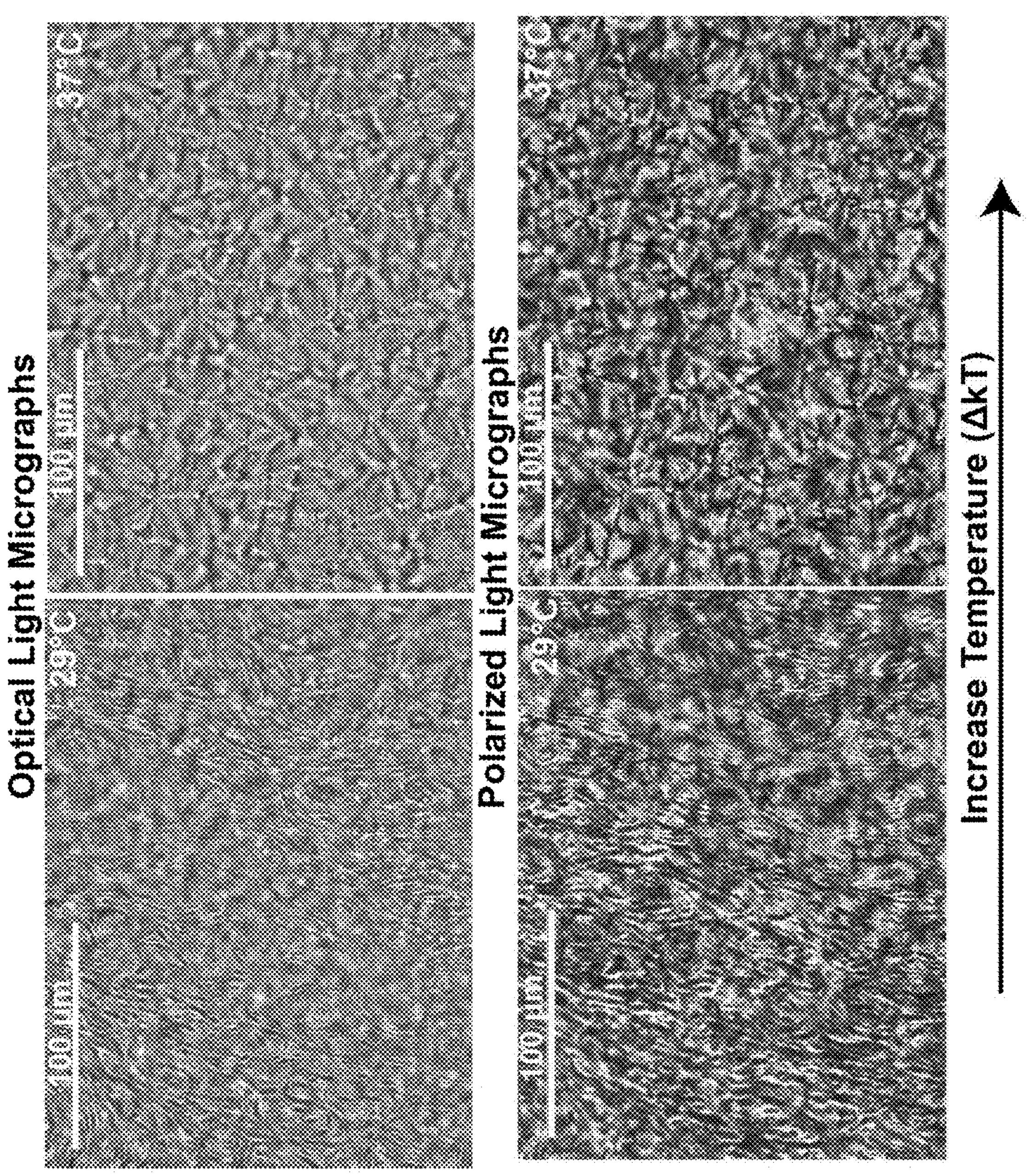
FIG. 11 depicts representative optical and polarized light micrographs of CLC.
Figure 12:
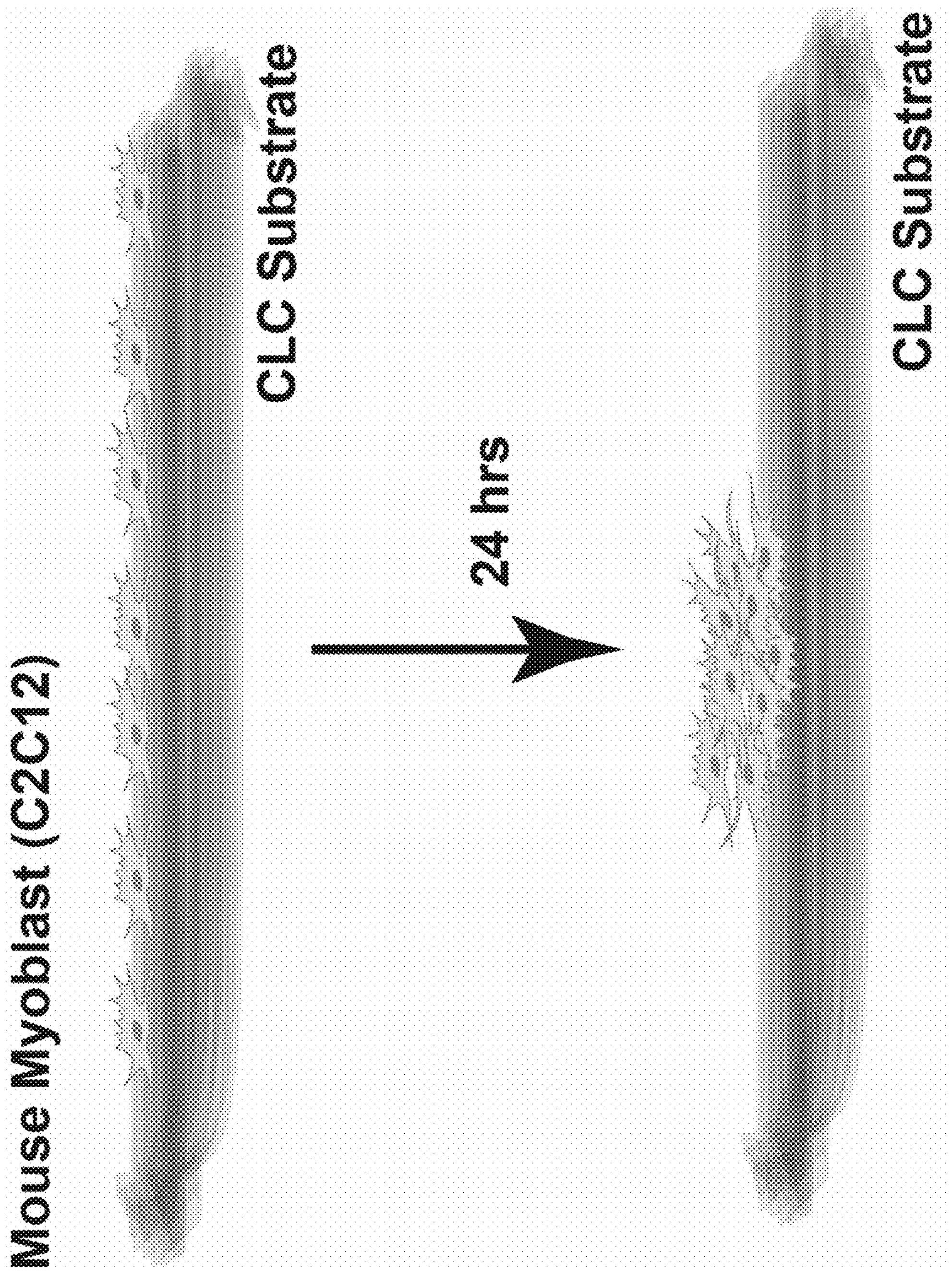
FIG. 12 depicts a schematic representation of organoid formation on CLC substrate.
Figure 13:
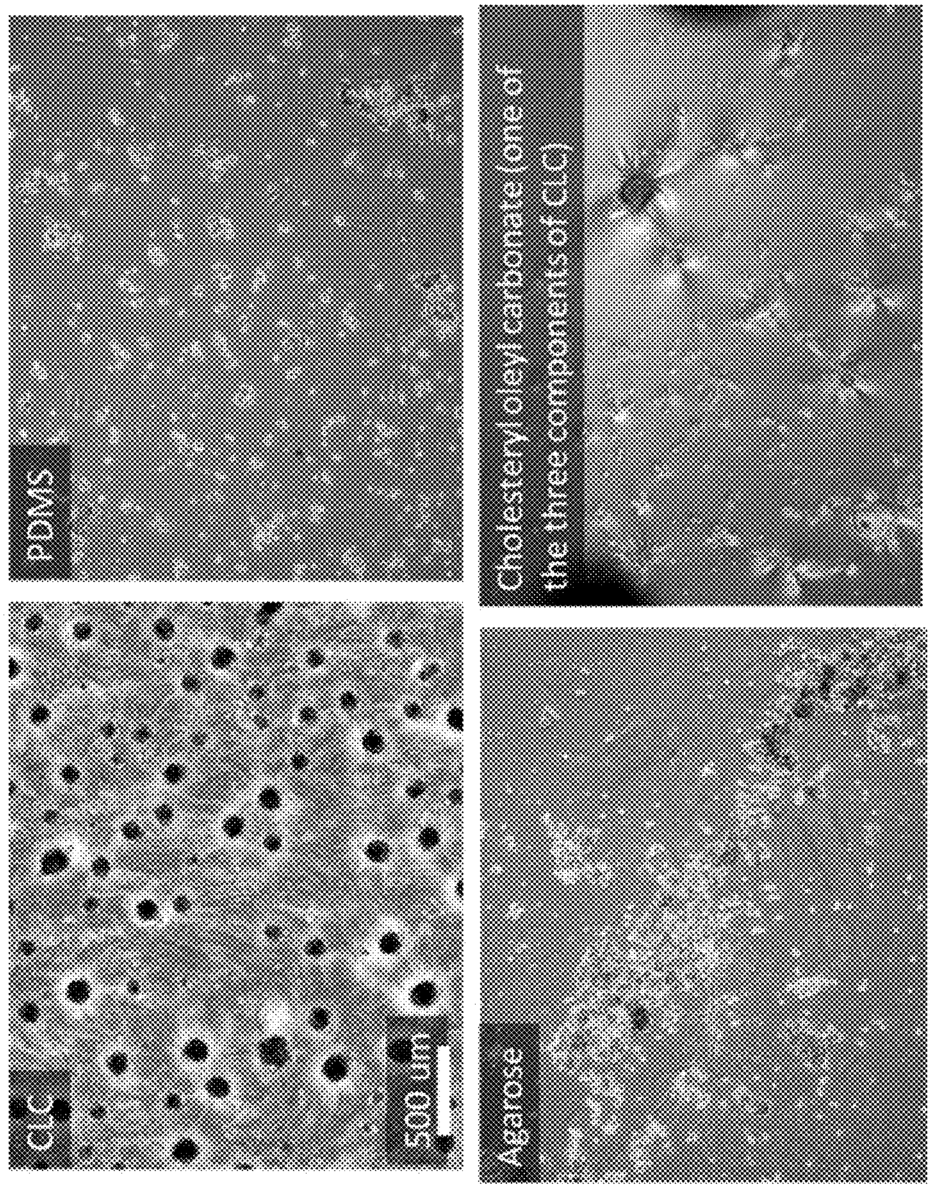
FIG. 13 depicts representative results demonstrating that cell growth was only observed on CLC substrate when compared to polydimethylsiloxane (PDMS), agarose, or cholesteryl oleyl carbonate substrates.
Figure 14:
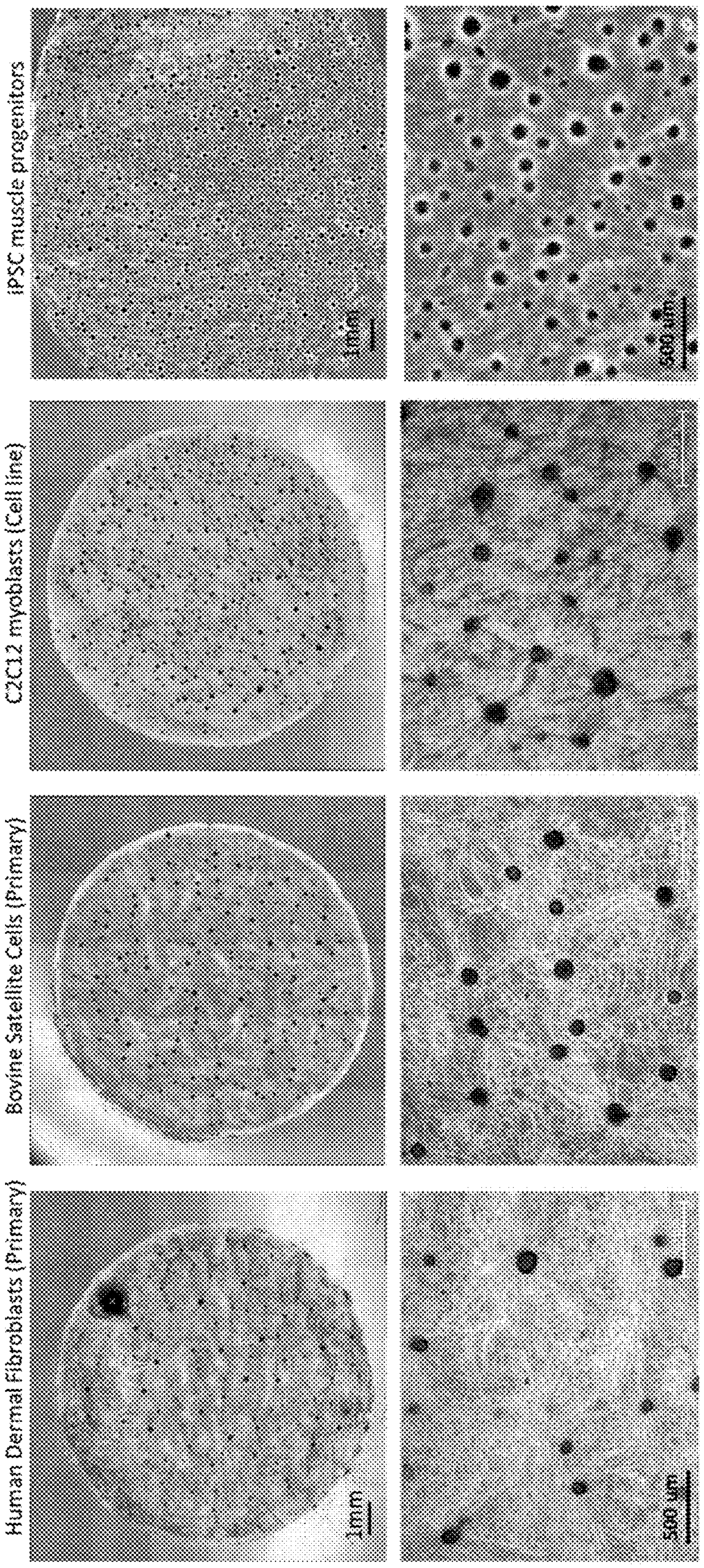
FIG. 14 depicts representative results of human dermal fibroblasts, bovine satellite cells, C2C12 myoblasts, and iPSC muscle progenitors growth.
Figure 15:
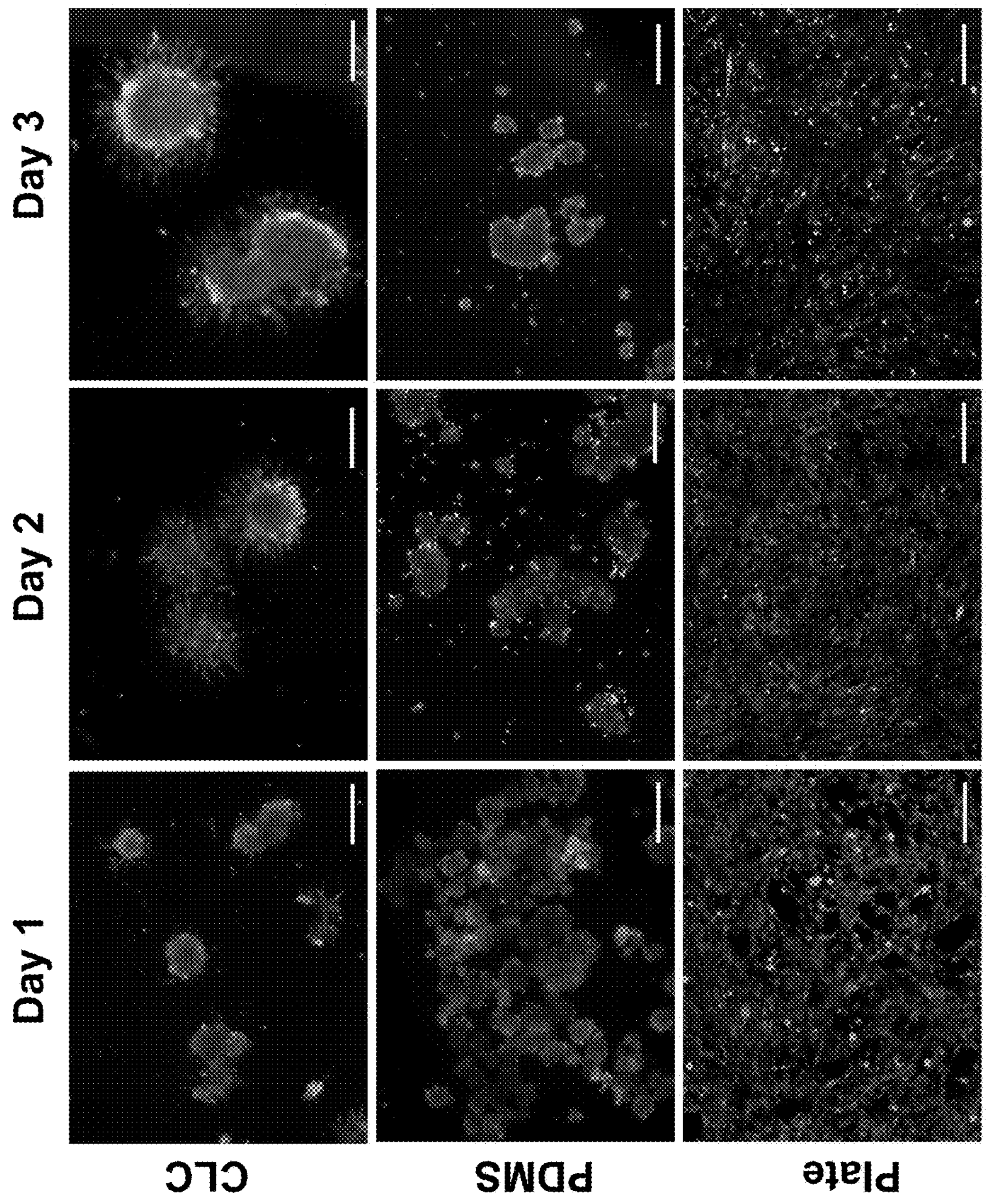
FIG. 15 depicts representative confocal images describing the cellular attachment on the CLC scaffold relative to a control PDMS.
Figure 16:
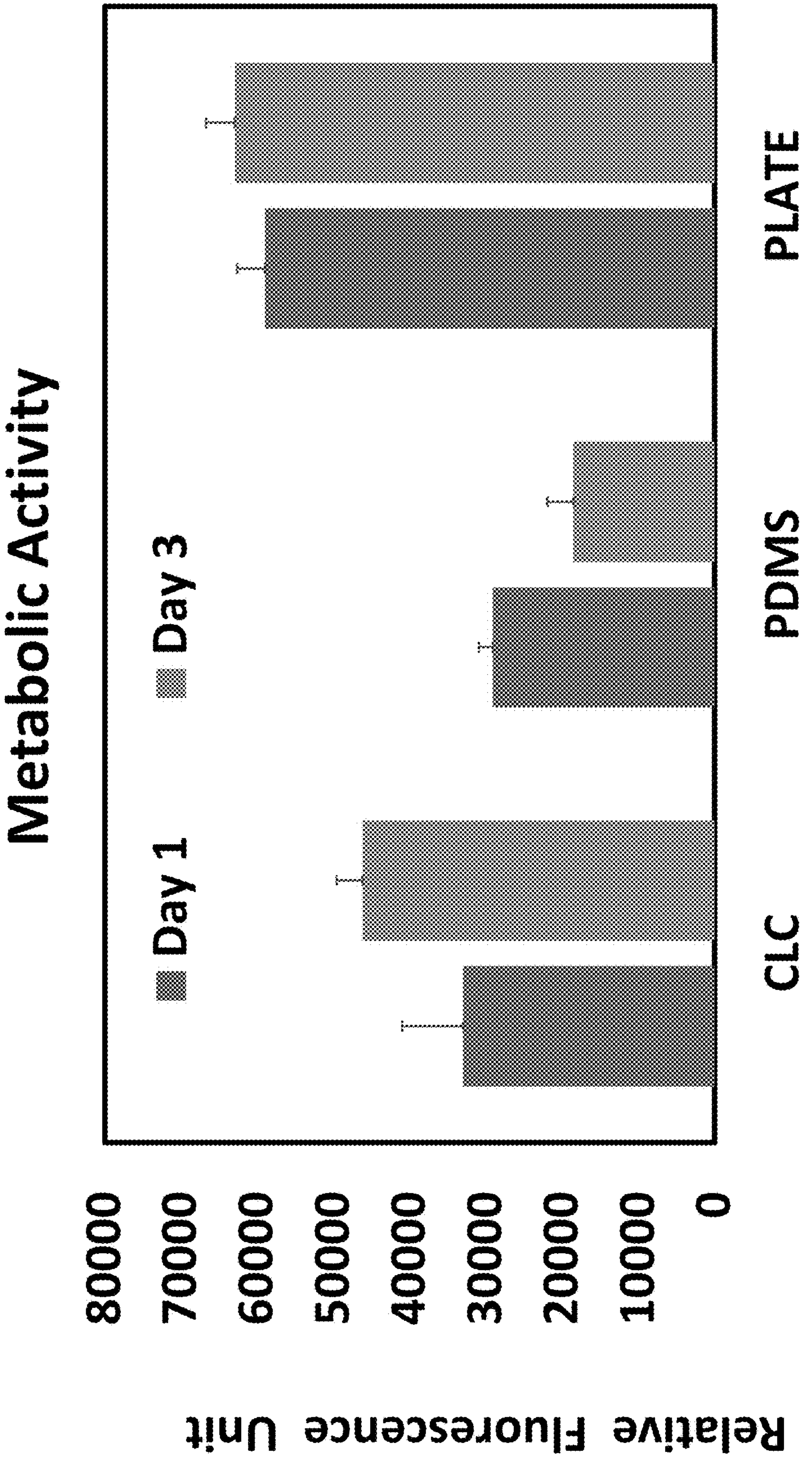
FIG. 16 depicts representative results demonstrating the metabolic activity on the CLC scaffold relative to a control PDMS.
Figure 17:
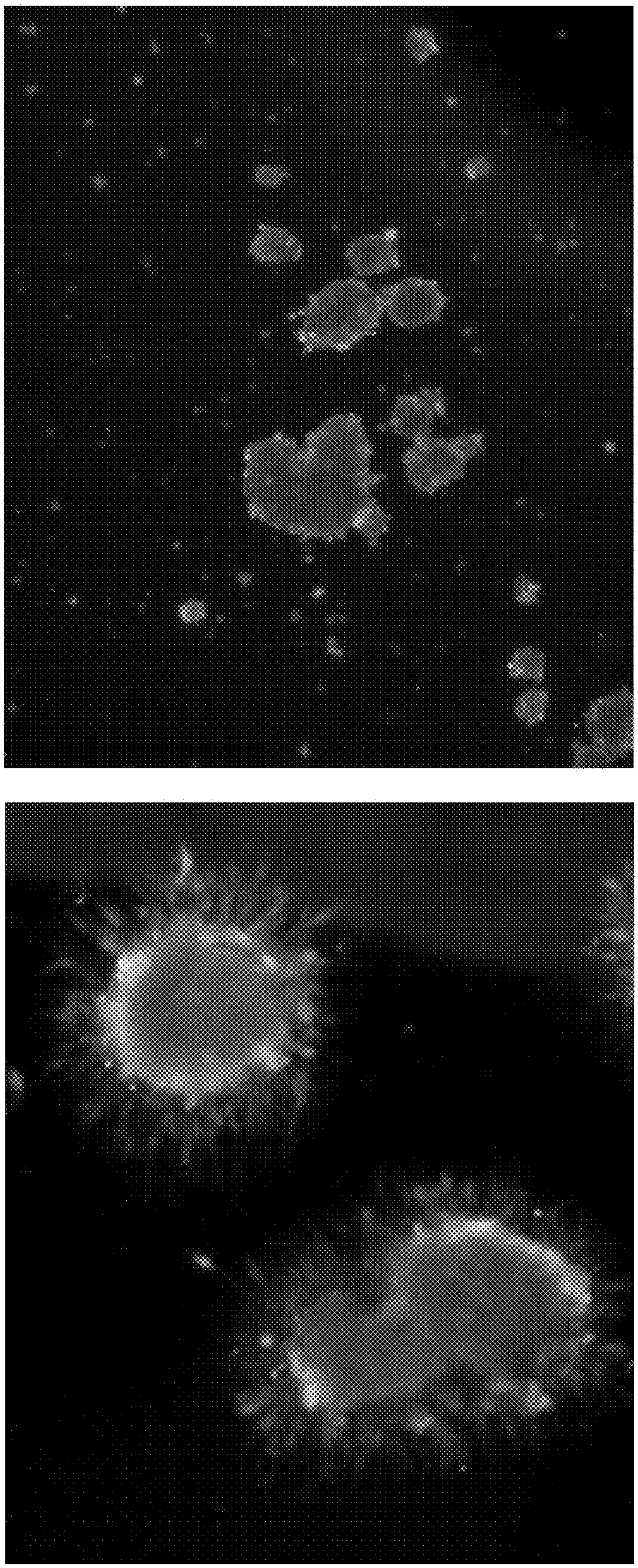
FIG. 17 depicts representative confocal images describing the cellular attachment on the CLC scaffold relative to a control PDMS.
Figure 18:
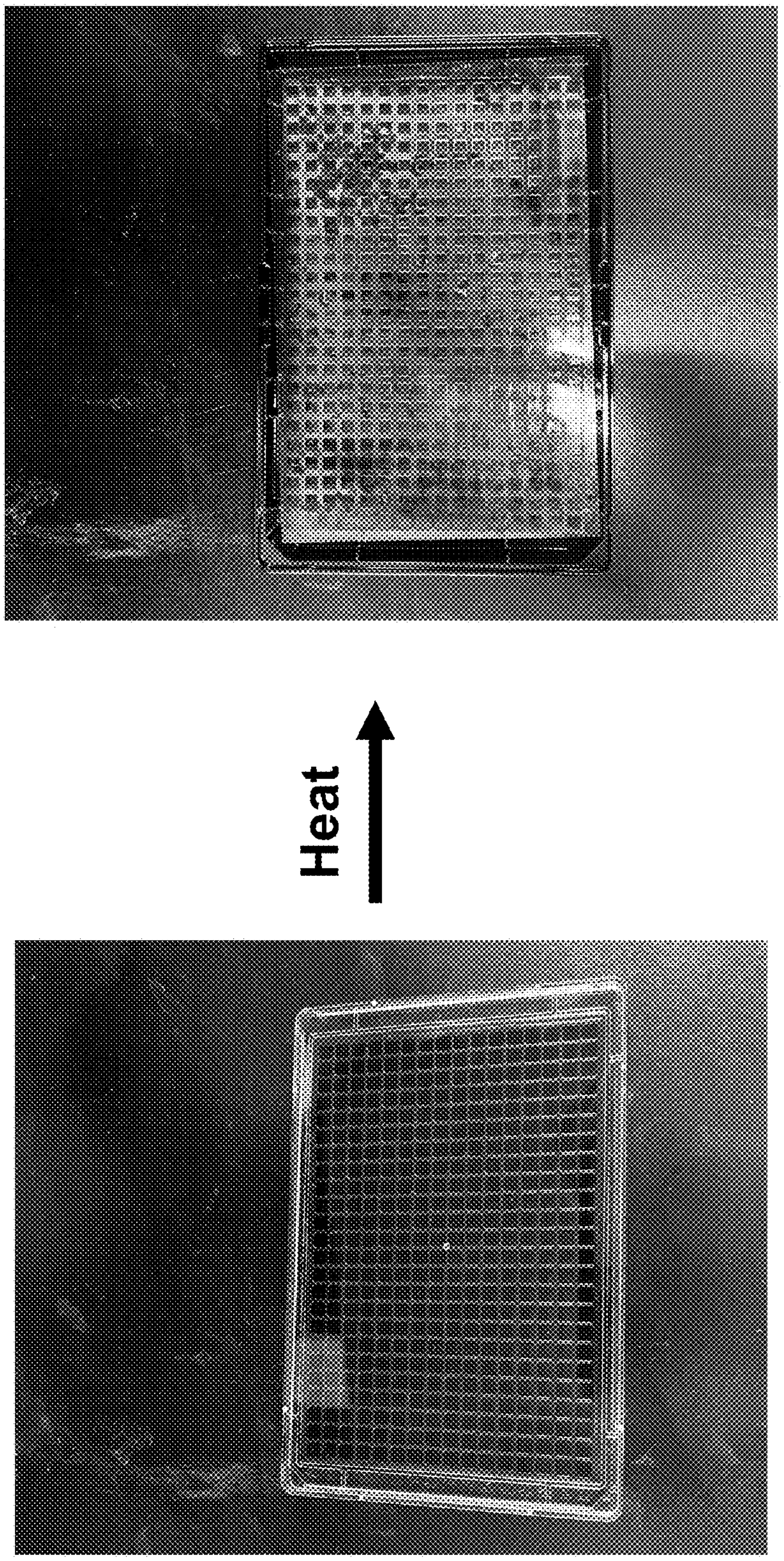
FIG. 18 depicts representative results demonstrating how the CLC-coated 96 well plates created high throughput organoid cultures for cancer diagnosis

The present invention is based, in part, on the discovery of novel methods of inducing generation of organoids, spheroids, and three-dimensional (3D) cellular aggregates using a biocompatible cholesteric liquid crystal (CLC) biomaterial. Thus, the present invention is directed, in part, to methods of inducing cell-culturing using a liquid crystal or a composition thereof (e.g., liquid crystal scaffold). The present invention is also directed, in part, to a method of manufacturing an organoid (e.g., a tumor organoid). In another aspect, the present invention relates to a method of manufacturing a spheroid (e.g., a tumor spheroid). In another aspect, the present invention relates to a method of manufacturing a 3D cell aggregate. In various embodiments, the method comprises culturing at least one cell on a liquid crystal (e.g., CLC) or a composition thereof (e.g., CLC-based scaffold).

In some aspects, the present invention also provides a method of evaluating a cancer treatment, wherein the method comprises a) manufacturing at least one tumor organoid or spheroid using the method of the present invention; b) applying the cancer treatment to the tumor organoid or spheroid; c) measuring a variable (e.g., size, viability, etc.) of the tumor organoid or spheroid; and d) determining the cancer treatment is effective when the variable (e.g., size, viability, etc.) of the tumor organoid or spheroid decreased when compared to a comparator.

In some aspects, the present invention also provides a cell culturing device comprising a liquid crystal or a composition thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "derivative" refers to a small molecule that differs in structure from the reference molecule, but retains the essential properties of the reference molecule. A derivative may change its interaction with certain other molecules relative to the reference molecule. A derivative molecule may also include a salt, an adduct, tautomer, isomer, or other variant of the reference molecule.

The term "tautomers" are constitutional isomers of organic compounds that readily interconvert by a chemical process (tautomerization).

The term "isomers" or "stereoisomers" refer to compounds, which have identical chemical constitution, but differ with regard to the arrangement of the atoms or groups in space.

As used herein, the terms "material" and "materials" refer to, in their broadest sense, any composition of matter.

As used herein, the term "substrate" refers to a solid object or support upon which another material is layered or attached. Solid supports include, but are not limited to, glass, metals, gels, and filter paper, among others.

As used herein, the term "mesogen" refers compounds that form liquid crystals, and in particular rigid rodlike or disclike molecules which are components of liquid crystalline materials.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, "thermotropic liquid crystal" refers to liquid crystals that result from the melting of mesogenic solids due to an increase in temperature. Both pure substances and mixtures form thermotropic liquid crystals.

The term "lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant, as is the case for nematics, the director rotates in a helical fashion throughout the sample. Chiral nematic crystals show a strong optical activity, which is much higher than can be explained on the basis of the rotatory power of the individual mesogens. When light equal in wavelength to the pitch of the director impinges on the liquid crystal, the director acts like a diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals that are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect X-rays.

"Discotic phases" are formed from molecules which are disc shaped rather than elongated. Usually, these molecules have aromatic cores and six lateral substituents. If the molecules are chiral, a chiral nematic discotic phase can form.

As used herein, the term "transparent" may refer to a material that permits at least 50% of the incident electromagnetic radiation at relevant wavelengths to be transmitted through it. In a device comprising a liquid crystal surface of the present invention, it may be desirable to allow the maximum amount of ambient electromagnetic radiation from the device exterior to be admitted to the liquid crystal layer region of the device. That is, the electromagnetic radiation must reach a liquid crystal layer(s), where it can stimulate the color change of the liquid crystal layer. This often dictates that at least one of the substrates of the device should be minimally absorbing and minimally reflecting of the incident electromagnetic radiation. In some cases, such a contact should be transparent or at least semi-transparent.

As used herein, the term "semi-transparent" may refer to a material that permits some, but less than 50% transmission of ambient electromagnetic radiation in relevant wavelengths. Where a transparent or semi-transparent substrate is used, the opposing substrate may be a reflective material so that light which has passed through the liquid crystal layer without being stimulating the color change of the liquid crystal layer is reflected back through the liquid crystal layer.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, "surface", "top surface", and "external surface" of the substrate are used interchangeably and refer to the surface of the substrate furthest away from the liquid crystal layer, while "bottom surface" or "internal surface" of the substrate are used interchangeably and refer to the surface of the substrate closest to the liquid crystal layer. Where a first layer is described as "disposed over" a second layer, the first layer is disposed further away from the external surface of the substrate. There may be other layers between the first and second layer, unless it is specified that the first layer is "in contact with" the second layer. For example, a liquid crystal layer may be described as "disposed over" at least a portion of the internal surface of the substrate, even though there are various organic layers in between.

As used and depicted herein, a "layer", for example a liquid crystal layer, refers to a member or component of a device being principally defined by a thickness, for example in relation to other neighboring layers, and extending outward in length and width. It should be understood that the term "layer" is not necessarily limited to single layers or sheets of materials. In addition, it should be understood that the surfaces of certain layers, including the interface(s) of such layers with other material(s) or layers(s), may be imperfect, wherein said surfaces represent an interpenetrating, entangled or convoluted network with other material(s) or layer(s). Similarly, it should also be understood that a layer may be uniform or discontinuous, such that the continuity of said layer along the length and width may be disturbed or otherwise interrupted by other layer(s) or material(s).

The terms "coat," "coated," or "coating," as used herein, refer to at least a partial coating of the surface of the substrate. One hundred percent coverage is not necessarily implied by these terms.

As used herein, "spin coating" may refer to the process of solution depositing a layer or film of one material (i.e., the coating material) on a surface of the device. The spin coating process may include applying a small amount of the coating material on the center of the substrate, which is either spinning at low speed or not spinning at all. The substrate is then rotated at high speed in order to spread the coating material by centrifugal force. Rotation is continued while the fluid spins off the edges of the substrate, until the desired thickness of the film is achieved. The higher the angular speed of spinning, the thinner the film. The thickness of the film also depends on the viscosity of the liquid crystal mesogen.

The terms "electrospinning" or "electrospun", as used herein refer to any method where materials are streamed, sprayed, sputtered, dripped, or otherwise transported in the presence of an electric field. The electrospun material can be deposited from the direction of a charged container towards a grounded target, or from a grounded container in the direction of a charged target. In particular, the term "electrospinning" means a process in which fibers are formed from a charged solution comprising at least one natural biological material, at least one synthetic polymer material, or a combination thereof by streaming the electrically charged solution through an opening or orifice towards a grounded template. As used herein, the terms "solution", "solvent", and "fluid" refer to a liquid that is capable of being charged and which comprises at least one natural material, at least one synthetic polymer, or a combination thereof.

The term "scaffold", as used herein, refers to any material that allows attachment of cells, preferably attachment of cells involved in meat growth or wound healing.

"Attachment", "attach" or "attaches" as used herein, refers to cells that adhere directly or indirectly to a substrate as well as to cells that adhere to other cells. Preferably the scaffold is three dimensional.

As used herein, the term "stem cell niche" refers to a cavity within an electrospun scaffold capable of housing one or more cells, e.g., stem cells, therein and providing a sheltering environment that physically protects said cells from physical disturbance and/or from stimulus that may promote differentiation and apoptosis. Preferably, the niche is a cavity defined by a concave surface within an electrospun scaffold, for example in the form of a pocket, a recess, a groove or a ridge.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nm) but greater than that of X-rays (i.e., greater than approximately 0.1 nm). Ultraviolet radiation possesses greater energy than visible light and is therefore, more effective at inducing photochemical reactions.

As used herein, the term "solvent" describes a liquid that serves as the medium for a reaction or a medium for the distribution of components of different phases or extraction of components into said solvent. Also, as used herein, the term "solvent" is intended to encompass liquids in which the raw materials or the reaction mixture are dispersed, suspended, or at least partially solvated. Examples of solvents include, but are not limited to, alcohols, ethers, acetones, DMSO, DMF, benzene, toluene, chloroform, dichloromethane, and hexanes.

As used herein, the terms "solvent-free", "at least substantially solvent-free", "at least substantially free of a solvent", and other like variants are used interchangeably to mean that no solvent is intentionally added to, or used in, any raw material or the reaction mixture (which includes all of the raw materials) during any of the processing steps leading to the formation of the metallic silver. It is to be understood that a raw material or reaction mixture that is at least substantially free of a solvent may inadvertently contain small amounts of a solvent owing to contamination or it may contain no amount of solvent.

As used herein the term "degradation" relates to the breakdown of the polymer structure of the scaffold. This breakdown of structural integrity is accompanied by the release from the scaffold of degradation products from the polymer and a reduction in the mechanical strength of the scaffold.

As used herein, the term "biodegradable" refers to material or polymer that can be degraded, preferably adsorbed and degraded in a patient's body. Preferably the scaffold is biodegradable, i.e., is formed of biodegradable materials, such as biodegradable polymers or naturally occurring biological materials.

As used herein, the terms "biocompatible" and "biologically compatible" are used interchangeably to the ability of a material, i.e., a polymer, to be implanted into or be administered to a human or animal body, without eliciting any undesirable local or systemic effects in the recipient, for example, without eliciting significant inflammation and/or acute rejection of the polymer by the immune system, for instance, via a T-cell response.

The term "organoid" as used herein refers to an agglomeration of cells that recapitulates aspects of cellular self-organization, architecture, and signaling interactions present in a native organ. The term "organoid" includes spheroids or cell clusters formed from suspension cell cultures.

As used herein, the term "spheroid" refers to microtissues of cells growing and/or interacting within their surroundings in all three dimensions in an artificially-created environment. Such microtissues can comprise a plurality of homotypic or heterotypic cells, preferably mammalian cells, more preferably human cells.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part, on the discovery of novel methods of inducing generation of organoids, spheroids, and three-dimensional (3D) cellular aggregates using a biocompatible cholesteric liquid crystal (CLC) biomaterial. Thus, the present invention is directed, in part, to methods of inducing cell-culturing using a liquid crystal or a composition thereof (e.g., liquid crystal scaffold). The present invention is also directed, in part, to a method of manufacturing an organoid (e.g., a tumor organoid). In another aspect, the present invention relates to a method of manufacturing a spheroid (e.g., a tumor spheroid). In another aspect, the present invention relates to a method of manufacturing a 3D cell aggregate. In various embodiments, the method comprises culturing at least one cell on a liquid crystal (e.g., CLC) or a composition thereof (e.g., CLC-based scaffold).

In some aspects, the present invention also provides a method of evaluating a cancer treatment, wherein the method comprises a) manufacturing at least one tumor organoid or spheroid using the method of the present invention; b) applying the cancer treatment to the tumor organoid or spheroid; c) measuring a variable (e.g., size, viability, etc.) of the tumor organoid or spheroid; and d) determining the cancer treatment is effective when the variable (e.g., size, viability, etc.) of the tumor organoid or spheroid decreased when compared to a comparator.

In some aspects, the present invention also provides a cell culturing device comprising a liquid crystal or a composition thereof.

Methods of Manufacturing 3D Cell Aggregate, Organoid, and/or Spheroid

The present invention provides a method of manufacturing a 3D cell aggregate. In some embodiments, the method comprises culturing at least one anchorage-dependent cell in the presence of a liquid crystal or a composition thereof.

In some embodiments, the 3D cell aggregate comprises any 3D cell aggregate known in the art. Examples of such 3D cell aggregate include, but are not limited to, a spheroid, a tumor spheroid, a stem cell spheroid, an organoid, a tumor organoid, a meat organoid, a fish organoid, an insulin generating organoid, a milk generating organoid, a blood generating organoid, a blood cell organoid, a blood product generating organoid, an extracellular matrix organoid, a stem cell organoid, a mixture of cells and biomaterials, polymers, lipids, phospholipids, proteins, or drugs, or any combination thereof.

In some embodiments, the method comprises culturing the at least one anchorage-dependent cell in the liquid crystal or composition thereof, on a surface of the liquid crystal or composition thereof, or both.

In some embodiments, the at least one anchorage-dependent cell comprises any anchorage-dependent cell of known in the art. Examples of such anchorage-dependent cell include, but are not limited to, a cancer cell, an epithelial cell, an endothelial cell, a fibroblast, a muscle cell, a myoblast cell, a neuron, an adipocyte, a cardiac cell, a hematopoietic a stem cell, a bone marrow cell, a gland cell, a mammary gland cell, a human mammary gland cell, an epidermal cell, a keratinocyte, a lactocytes, a hepatic cell, a beta cells pancreatic cell, a human cell, a mammalian cell, a vertebrate cell, an invertebrate cell, a bacterial cell, a human dermal fibroblast, a human keratinocyte, a human epidermal cell, a human cancer cell, a human brain cancer cell, a bovine satellite cell, a C2C12 myoblast, an induced pluripotent stem cell (iPSC), a mesenchymal stem cell (MSC), an iPSC muscle progenitor, or any combination thereof.

In another aspect, the present invention provides a method of manufacturing an organoid. In some embodiments, the organoid is selected from a tumor organoid, meat organoid, fish organoid, insulin generating organoid, milk generating organoid, blood generating organoid, blood cell organoid, blood product generating organoid, extracellular matrix organoid, stem cell organoid, or any combination thereof. For example, in one embodiment, the organoid is a tumor organoid.

In another aspect, the present invention relates to a method of manufacturing a spheroid. In some embodiments, the spheroid is selected from a tumor spheroid, stem cell spheroid, or any combination thereof. For example, in one embodiment, the spheroid is a tumor spheroid.

In another aspect, the present invention relates to a method of manufacturing a 3D cell aggregate.

In another aspect, the present invention relates to a method of co-culturing at least one cell with at least one second cell. For example, in some embodiments, the present invention relates to a method of co-culturing at least one anchorage-dependent cell with at least one second cell.

In some embodiments, the method comprises co-culturing the cells in the presence of a liquid crystal or a composition thereof.

In some embodiments, the method comprises at least one of controlling organization, ordering addition of the cells, and cell-directing organization of the cells.

In some embodiments, the method comprises controlled organization. In one embodiment, the organization is a core-shell organization. In some embodiments, the cells are co-cultured to form a core-shell organization.

In some embodiments, the cells are co-cultured at the same time to make a cell-directed organization of the cells.

In some embodiments, the method comprises ordered addition of the cells.

In various embodiments, the method comprises culturing at least one cell in the presence of a liquid crystal or a composition thereof. In some embodiments, the method comprises culturing at least one cell in a liquid crystal or a composition thereof. In some embodiments, the method comprises culturing at least one cell on a surface of a liquid crystal or a composition thereof. In some embodiments, the method comprises culturing at least one cell on a surface of a liquid crystal or a composition thereof to form a 3D cell culture.

In various embodiments, the cell comprises any cell of interest. Examples of such cell of interest include, but are not limited to, a cancer cell, tissue cell, epithelial cell, endothelial cell, fibroblast, muscle cell, myoblast cell, neuron, adipocyte, cardiac cell, stem cell (e.g., a muscle stem cell, mesenchymal stem cell, epithelial stem cell, etc.), fat cells, hematopoietic stem cell, bone marrow cell, gland cell, mammary gland cell, human mammary gland cell, epidermal cell, keratinocyte, bovine satellite cell, lactocytes, hepatic cell, beta cells pancreatic cell, C2C12 myoblast, iPSC, MSC, iPSC muscle progenitor, or any combination thereof.

In some embodiments, the cell is selected from a human cell, mammalian cell, vertebrate cell, invertebrate cell, bacterial cell, or any combination thereof.

In some embodiments, the cell is a mammalian cell (e.g., human cell, canine cell, feline cell, bovine cell, swine/porcine cell, sheep cell, goat cell, horse cell, etc.), avian cell (e.g., chicken cell, duck cell, turkey cell, quail cell, etc.), piscine muscle cell (e.g., tuna cell, salmon cell, snapper cell, cod cell, etc.), shellfish cell (e.g., lobster cell, crab cell, shrimp cell, crayfish cell, clam cell, oyster cell, mussel cell, etc.), or any combination thereof.

For example, in some embodiments, the cell is a cancer cell, human dermal fibroblast, human cancer cell, human brain cancer cell, human keratinocyte, human epidermal cell, cardiac cell, bovine satellite cell, C2C12 myoblast, iPSC, MSC, iPSC muscle progenitor, or any combination thereof.

In various embodiments, the present invention provides a method of generating a synthetic tumor (e.g., tumor organoid, tumor spheroid, etc.).

In some embodiments, the liquid crystal or the composition thereof is a liquid crystal or a composition thereof for inducing and/or propagating cellular agriculture of at least one cell or cell tissue layer of interest.

In various embodiments, the liquid crystal comprises cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof. For example, in some embodiments, the liquid crystal or composition thereof comprises at least one selected from the group consisting of cholesteryl oleyl carbonate or a derivative thereof, cholesteryl pelargonate or a derivative thereof, and cholesteryl benzoate or a derivative thereof. Thus, in some embodiments, the liquid crystal comprises a cholesteryl ester liquid crystal. In some embodiments, the liquid crystal is a cholesteryl ester liquid crystal.

In some embodiments, the liquid crystal comprises a cellulose-based liquid crystal. In some embodiments, the liquid crystal is a cellulose-based liquid crystal.

In some embodiments, the liquid crystal comprises between about 50 mg to about 2000 mg cholesteryl oleyl carbonate or a derivative or a salt thereof, between about 50 mg to about 2000 mg cholesteryl pelargonate or a derivative or a salt thereof, between about 50 mg to about 2000 mg cholesteryl benzoate or a derivative or a salt thereof, between about 50 mg to about 2000 mg cellulose or a derivative or a salt thereof, or any combination thereof. For example, in one embodiment, the liquid crystal comprises about 320 mg cholesteryl oleyl carbonate or a derivative or a salt thereof, about 580 mg cholesteryl pelargonate or a derivative or a salt thereof, about 100 mg cholesteryl benzoate or a derivative or a salt thereof, or any combination thereof. In another embodiment, the liquid crystal comprises about 480 mg cholesteryl oleyl carbonate or a derivative or a salt thereof, about 870 mg cholesteryl pelargonate or a derivative or a salt thereof, about 150 mg cholesteryl benzoate or a derivative or a salt thereof, or any combination thereof. In yet another embodiment, the liquid crystal comprises about 640 mg cholesteryl oleyl carbonate or a derivative or a salt thereof, about 1160 mg cholesteryl pelargonate or a derivative or a salt thereof, about 200 mg cholesteryl benzoate or a derivative or a salt thereof, or any combination thereof.

In other embodiments, the liquid crystal comprises synthetic polyurethane lacquer, natural lacquer derived from catechol molecules, urushiol mixtures, or any combination thereof.

In some embodiments, the liquid crystal or composition thereof displays a phase change between about 10° C. and about 60° C. In some embodiments, the liquid crystal or composition thereof displays a phase change between about 17° C. and about 40° C. In some embodiments, the liquid crystal or composition thereof displays a phase change between about 32° C. and about 42° C. In some embodiments, the liquid crystal or composition thereof displays a phase change between about 32° C. and about 40° C. In some embodiments, the liquid crystal or composition thereof displays a phase change between about 34° C. and about 48° C. In some embodiments, the liquid crystal or composition thereof displays a phase change between about 36° C. and about 40° C. In some embodiments, the liquid crystal or composition thereof displays a phase change at about 37° C.

In some embodiments, the liquid crystal has a mesophase between about 10° C. and about 60° C. In some embodiments, the liquid crystal has a mesophase between about 17° C. and about 40° C. In some embodiments, the liquid crystal has a mesophase between about 32° C. and about 42° C. In some embodiments, the liquid crystal has a mesophase between about 32° C. and about 40° C. In some embodiments, the liquid crystal has a mesophase between about 34° C. and about 48° C. In some embodiments, the liquid crystal has a mesophase between about 36° C. and about 40° C. In some embodiments, the liquid crystal has a mesophase at about 37° C.

In some embodiments, the liquid crystal forms striations between about 10° C. and about 60° C. In some embodiments, the liquid crystal forms striations at a temperature between about 17° C. and about 40° C. In some embodiments, the liquid crystal forms striations at a temperature between about 32° C. and about 42° C. In some embodiments, the liquid crystal forms striations at a temperature between about 32° C. and about 40° C. In some embodiments, the liquid crystal forms striations at a temperature between about 34° C. and about 38° C. In some embodiments, the liquid crystal forms striations at a temperature between about 36° C. and about 40° C. In some embodiments, the liquid crystal forms striations at a temperature about 37° C.

In various embodiments, the liquid crystal comprises a mesogenic layer. In one embodiment, the liquid crystal comprises a mesogenic layer comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof. In another embodiment, any compound or mixture of compounds that form a mesogenic layer can be used in conjunction with the present invention.

The mesogens can form thermotropic or lyotropic liquid crystals. The mesogenic layer can be either continuous or it can be patterned. Both the thermotropic and lyotropic liquid crystals can exist in a number of forms including nematic, chiral nematic, smectic, polar smectic, chiral smectic, frustrated phases and discotic phases.

The mesogenic layer can be a substantially pure compound, or it can contain other compounds that enhance or alter characteristics of the mesogen. Thus, in one embodiment, the mesogenic layer further comprises a second compound, for example an alkane, which expands the temperature range over which the nematic and isotropic phases exist.

In some embodiments, the mesogenic layer further comprises a dichroic dye or fluorescent compound. Examples of dichroic dyes and fluorescent compounds useful in the present invention include, but are not limited to, azobenzene, BTBP, polyazocompounds, anthraquinone, perylene dyes, and the like. In some embodiments, a dichroic dye of fluorescent compound is selected that complements the orientation dependence of the liquid crystal so that polarized light is not required for the device of the present invention to show different colors. In some embodiments, if the absorbance of the liquid crystal is in the visible range, then changes in orientation can be observed using ambient light without crossed polarizers. In other embodiments, the dichroic dye or fluorescent compound is used in combination with a fluorimeter and the changes in fluorescence are used to detect changes in orientation of the liquid crystal.

In various embodiments, the liquid crystal is a molecular switch. In one embodiment, the liquid crystal changes color when exposed to a stimulus. In various embodiments, the mesogenic layers of the instant invention can be tuned by the use of at least one stimulus. In some embodiments, the stimulus comprises applying energy or a pH change to the device. Examples of such stimulus include, but are not limited to temperature, electric field (e.g., voltage), electromagnetic field, magnetic field, light, optical methods (e.g., ultraviolet (UV) irradiation, UV-vis-NIR irradiation, infrared (IR) irradiation, NIR irradiation), radiofrequencies, radiation, sound, hydration, pH, pressure, or any combination thereof.

In one embodiment, the stimulus is used to reversibly orient the mesogenic layer. In one embodiment, the stimulus is applied either perpendicular to, or in the plane of, the surface of the mesogenic layer. In one embodiment, the oriented mesogenic layer modulates the intensity of light diffracted from the layer.

For example, in one embodiment the mesogenic layers of the instant invention can be tuned by the use of electric fields. In one embodiment, the electric field is used to reversibly orient the mesogenic layer. In one embodiment, the electric field is applied either perpendicular to, or in the plane of, the surface of the mesogenic layer. In one embodiment, the oriented mesogenic layer modulates the intensity of light diffracted from the layer.

In another embodiment the mesogenic layers of the instant invention can be tuned by the use of temperature (e.g., heat). In one embodiment, the temperature (e.g., heat) is used to reversibly orient the mesogenic layer. In one embodiment, the temperature (e.g., heat) is applied either perpendicular to, or in the plane of, the surface of the mesogenic layer. In one embodiment, the oriented mesogenic layer modulates the intensity of light diffracted from the layer.

In another embodiment, the mesogenic layer is subsequently cooled to form the liquid crystalline phase. The presence of the stimulus within regions of the mesogenic layer will disturb the equilibrium between the nematic and isotropic phases leading to different rates and magnitudes of nucleation at those sites. The differences between the nematic and isotropic regions are clearly detectable.

When the liquid crystal is exposed to the stimulus, the orientation of the liquid crystal is disrupted. In some embodiments, the disruption of orientation can be detected by a variety of methods, including detecting a color change of the liquid crystal, viewing with crossed polarizers, measuring the threshold electrical field required to change the orientation of the liquid crystal, viewing in the presence of dichroic agents, or any combination thereof. The liquid crystals can be viewed using white light or using a specific wavelength or combination of wavelengths of light.

Although many changes in the mesogenic layer can be detected by visual observation under ambient light, any means for detecting the change in the mesogenic layer can be incorporated into, or used in conjunction with, the device. Thus, it is within the scope of the present invention to use lights, microscopes, spectrometry, electrical techniques and the like to aid in the detection of a change in the mesogenic layer.

In those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device such as that described in U.S. Pat. No. 5,739,879, incorporated herein by reference. Light in the ultraviolet and infrared regions is also of use in the present invention.

The present invention also relates, in part, to the use of plate readers to detect changes in the orientation of mesogens. The plate readers may be used in conjunction with the LC assay devices described herein and also with the lyotropic LC assays described in U.S. Pat. No. 6,171,802, incorporated herein by reference. In particular, the present invention includes methods and processes for the quantification of light transmission through films of liquid crystals based on quantification of transmitted or reflected light.

In various embodiments, the composition comprises any liquid crystal described herein. For example, in some embodiments, the composition comprises a liquid crystal layer. In some embodiments, the composition comprises a uniformly oriented liquid crystal.

In various embodiments, the composition is a tunable composition. In some embodiments, the tunable composition permits the manipulation of light. In one embodiment, the composition is a refractive-diffractive device. In one embodiment, the composition permits imaging from a single optical element. In one embodiment, the composition permits aplanatic or chromatic correction in lenses. In one embodiment, the composition allows for spectral dispersion. Thus, for example, in one embodiment, the tunable composition changes color when exposed to a stimulus.

In some embodiments, the composition comprises at least one cell. Examples of such cell include, but are not limited to a tissue cell, epithelial cell, endothelial cell, muscle cell, neuron, adipocyte, cardiac cell, stem cell (e.g., a muscle stem cell, mesenchymal stem cell, epithelial stem cell, etc.), fat cell, hematopoietic stem cell, bone marrow cell, gland cell, mammary gland cell, human mammary gland cell, epidermal cell, keratinocyte, bovine satellite cell, lactocytes, hepatic cell, beta cells pancreatic cell, C2C12 myoblast, iPSC, MSC, iPSC muscle progenitor, or any combination thereof.

In some embodiments, the composition comprises at least one component selected from a polymer, solvent, additive, substrate, composite, protein, or any combination thereof. In some embodiments, the composition comprises at least one component selected from a additive, substrate, composite, or any combination thereof.

In some embodiments, the at least one component is not covalently bound to the liquid crystal. In some embodiments, the at least one component is covalently bound to the liquid crystal. For example, in some embodiments, the composition comprises at least one component selected from a composite, substrate, cholesteryl ester liquid crystal-based scaffold, and additive, wherein the at least one component is not covalently bound to the liquid crystal.

In some embodiments, the composition comprises between about 5% (w/v) to between about 95% (w/v) liquid crystal. In some embodiments, the composition comprises between about 15% (w/v) to between about 85% (w/v) liquid crystal. In some embodiments, the composition comprises between about 25% (w/v) to between about 50% (w/v) liquid crystal. In one embodiment, the composition comprises about 25% (w/v) liquid crystal. In one embodiment, the composition comprises about 37% (w/v) liquid crystal. In one embodiment, the composition comprises about 50% (w/v) liquid crystal.

In some embodiments, the composition comprises between about 0.000001% (w/v) to between about 95% (w/v) polymer. In some embodiments, the composition comprises between about 15% (w/v) to between about 85% (w/v) polymer. In some embodiments, the composition comprises between about 15% (w/v) to between about 50% (w/v) polymer. In some embodiments, the composition comprises between about 0.000001% (w/v) to between about 1% (w/v) polymer. In one embodiment, the composition comprises about 15% (w/v) polymer.

In some embodiments, the composition comprises between about 5% (w/v) to between about 95% (w/v) solvent. In some embodiments, the composition comprises between about 15% (w/v) to between about 85% (w/v)

solvent. In some embodiments, the composition comprises between about 25% (w/v) to between about 50% (w/v) solvent. In one embodiment, the composition comprises about 85% (w/v) solvent.

In some embodiments, the composition comprises between about 0.05% (w/v) to between about 95% (w/v) additive. In some embodiments, the composition comprises between about 1.5% (w/v) to between about 85% (w/v) additive. In some embodiments, the composition comprises between about 2.5% (w/v) to between about 50% (w/v) additive. In one embodiment, the composition comprises about 0.25% (w/v) additive. In one embodiment, the composition comprises about 3% (w/v) additive. In one embodiment, the composition comprises about 5% (w/v) additive.

In some embodiments, the composition comprises between about 5% (w/v) to between about 95% (w/v) substrate. In some embodiments, the composition comprises between about 15% (w/v) to between about 85% (w/v) substrate. In some embodiments, the composition comprises between about 15% (w/v) to between about 50% (w/v) substrate. In one embodiment, the composition comprises about 15% (w/v) substrate.

In some embodiments, the composition comprises between about 5% (w/v) to between about 95% (w/v) composite (e.g., resin matrix). In some embodiments, the composition comprises between about 15% (w/v) to between about 85% (w/v) composite. In some embodiments, the composition comprises between about 15% (w/v) to between about 50% (w/v) composite. In one embodiment, the composition comprises about 15% (w/v) composite.

In some embodiments, the composition comprises between about 5% (w/v) to between about 95% (w/v) protein. In some embodiments, the composition comprises between about 15% (w/v) to between about 85% (w/v) protein. In some embodiments, the composition comprises between about 15% (w/v) to between about 50% (w/v) protein. In one embodiment, the composition comprises about 15% (w/v) protein.

In some embodiments, the solvent is a liquid in which the raw materials or the reaction mixture are dispersed, suspended, or at least partially solvated. Examples of solvents include, but are not limited to, alcohols, ethers, acetones, benzene, toluene, chloroform, dichloromethane, DMSO, and cyclohexanes.

In some embodiments, the composite is an organic-inorganic composite, nacre, glass composite, fiber composite, glass fiber composite, carbon composite, resin matrix, or any combination thereof.

In some embodiments, the polymer is a biodegradable polymer, biocompatible polymer, edible polymer, food grade polymer, plant-based polymer, animal-derived polymer, human-derived polymer, or any combination thereof.

In some embodiments, the polymer has molecular weight of 5 kDa-3000 kDa. For example, in one embodiment, the polymer has a molecular weight of 5 kDa-2000 kDa, 5 kDa-1500 kDa, 5 kDa-1000 kDa, 5 kDa-800 kDa, 5 kDa-500 kDa, 5 kDa-300 kDa or 5 kDa-200 kDa or 800 kDa-3000 kDa.

In some embodiments, the polymer is a straight chain polymer (i.e., linear polymer) or a branched chain polymer (i.e., branched polymer), including hyperbranched polymers. In some embodiments, the polymer is cross-linked. In one embodiment, the polymer is a fibrous network.

In some embodiments, the polymer is a neutral polymer, ionic polymer, anionic polymer, or cationic polymer.

In some embodiments, the polymer is a homopolymer, copolymer, or block copolymer. In some embodiments, the block copolymer is a triblock, tetrablock, pentablock, or at least six block copolymer.

In some embodiments, the polymer is polysaccharide, alginate, agar, polyester, polyolefin, poly(vinyl chloride), polystyrene, polycaprolactone, polyethylene, polycarbonate, polyalkyleneimine (e.g., polyethyleneimine), polyallylamine, polyamidoamine, or poly(amino-co-ester), or any combination thereof. Examples of polymers also include, but are not limited to poly(ethylene oxide) (PEO) block copolymer, polyacrylate, polymethacrylate, polyamine, polyalkyleneimine (e.g., polyethyleneimine), polyallylamine, polyamidoamine, polyolefin, poly(amino-co-ester), poly(ethylethylene) (PEE), polymethyl methacrylate (PMMA), polyethyleneimine (PEI), chitosan, poly(butadiene) (PB or PBD), poly(styrene) (PS), poly(isoprene) (PI), polyethyleneimine (PEI), poly(lactide-co-glycolic acid) (PLGA), biodegradable PLGA, polyethylene glycol (PEG), poly(lactide-co-glycolic acid)-polyethylene glycol (PLGA-PEG), poly (lactide-co-glycolic acid)-block-polyethylene glycol (PLGA-b-PEG), biodegradable PLGA-PEG, biodegradable PLGA-b-PEG, polyanhydride, polyanhydride-block-PEG copolymers, zwitterionic poly(carbobetaine), zwitterionic poly(sulfobetaine)-containing, zwitterionic poly(carbobetaine) and zwitterionic poly(sulfobetaine)-containing copolymers, poly(acrylic acid-co-distearin acrylate), poly (trimethylene carbonate)-block-poly(L-gluatamic acid), poly(ethylene glycol-block-L-aspartic acid), poly(2-hydroxyethyl-co-octadecyl aspartamide), poly(ethylene glycol-co-trimethylene carbonate-co-caprolactone, polypropylene oxide block copolymers, polyethylene oxide-block-polypropylene oxide copolymers, poly(ε-caprolactone) (PCL) diblock co-polymer, poly(ethylene oxide)-block-poly (ε-caprolactone) (PEO-b-PCL) based diblock copolymers, poly(lactic acid), poly(glycolide), poly(lactic-coglycolic acid), poly(3-hydroxybutyrate), poly(lactide-co-glycolic acid)-polyethylene glycol (PLGA-PEG), poly(lactide-co-glycolic acid)-block-polyethylene glycol (PLGA-b-PEG), chitosan, poly(2-N,N-dimethylaminoethylmethacrylate), poly-L-lysine, zein, alginate, hyaluronic acid, mycelium, or any combination thereof. For example, in one embodiment, the polymer is polycaprolactone.

In one embodiment, the polymer is an organic polymer. Examples of such organic polymers include, but are not limited to, polyalkenes (e.g., polyethylene, polyisobutene, polybutadiene), polyacrylics (e.g., polyacrylate, poly (methyl methacrylate), polycyanoacrylate), polyvinyls (e.g., poly(vinyl alcohol), poly(vinyl acetate), poly(vinyl butyral), poly(vinyl chloride)), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers, phenolic resins (e.g., Cognard, J. Alignment of Nematic Liquid Crystals and Their Mixtures, in Mol. Cryst. Liq. Cryst. 1:1-74 (1982)), polydimethylsiloxane, polyethylene, polyacrylonitrile, cellulosic materials, polycarbonates, poly(vinyl pyridinium), zein, alginate, hyaluronic acid, mycelium, or any combination thereof.

In one embodiment, the polymer is a synthetic polymer. A synthetic polymer material can be any material prepared through a method of artificial synthesis, processing, or manufacture. Both the biological and polymeric materials are capable of being charged under an electric field.

In one embodiment, the polymer is a biocompatible polymer.

In some embodiments, the polymer is a biocompatible synthetic polymer. Examples of biocompatible synthetic polymers include, but are not limited to, poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), polyvinyl alcohol) (PVA), poly(acrylic acid), polyvinyl acetate), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate)), polyvinylhydroxide, zein, alginate, hyaluronic acid, mycelium, poly(ethylene oxide) (PEO) and polyorthoesters or co-polymers thereof. In some embodiments, the biocompatible polymer is PGLA.

In one embodiment, the polymer is a biodegradable polymer. Examples of suitable biodegradable materials include, but are not limited to collagen, poly(alpha esters) such as poly(lactate acid), poly(glycolic acid), polyorthoesters, polyanhydrides polyglycolic acid and polyglactin, and copolymers thereof. Other suitable biodegradable polymers include cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, poly(vinylidene fluoride), regenerated cellulose, silicone, urea-formaldehyde, zein, alginate, hyaluronic acid, mycelium, or copolymers or thereof.

In some embodiments, the polymer is permeable to gases, liquids, molecules in solution, or any combination thereof. In some embodiments, the polymer is impermeable to gases, liquids, molecules in solution, or any combination thereof.

In one embodiment, the polymer is at least one polymer bead. In another embodiment, the polymer is a substrate.

In various embodiments, the polymer is a biomimetic interface.

In some embodiments, the polymer is a film of a thickness of from about 0.01 nanometer to about 10 centimeters. For example, in some embodiments, the polymer is a film of a thickness of from about 0.1 nanometer to about 10 millimeters. In some embodiments, the polymer is a film of a thickness of from about 0.1 nanometer to about 10 micrometers. In some embodiments, the polymer is a film of a thickness of from about 0.1 nanometer to about 10 nanometers. In some embodiments, the polymer is a film of a thickness of from about 0.1 nanometer to about 1 millimeter. In some embodiments, the polymer is a film of a thickness of from about 1 nanometer to about 10 millimeters. In some embodiments, the polymer is a film of a thickness of from about 1 nanometer to about 1 micrometer. In some embodiments, the polymer is a film of a thickness of from about 5 nanometers to about 100 nanometers. In some embodiments, the polymer is a film of a thickness of from about 10 nanometers to about 50 nanometers.

In some embodiments, the composition can be of any configuration that allows for the contact of a mesogenic layer with the substrate. In various embodiments, the liquid crystal layer is placed on the substrate by electrospinning, spin coating, electrospraying, airbrushing, brushing, 3D printing, or any combination thereof of a liquid crystal on the substrate.

In various embodiments, the liquid crystal layer is placed on the substrate in a solvent-free matter. For example, in some embodiments, the liquid crystal layer is placed on the substrate by solvent-free electrospinning, solvent-free spin coating, solvent-free electrospraying, solvent-free airbrushing, solvent-free brushing, solvent-free 3D printing, or any combination thereof of a liquid crystal on the substrate.

In various embodiments, the liquid crystal layer is placed on the substrate in a polymer-free matter. For example, in some embodiments, the liquid crystal layer is placed on the substrate by polymer-free electrospinning, polymer-free spin coating, polymer-free electrospraying, polymer-free airbrushing, polymer-free brushing, polymer-free 3D printing, or any combination thereof of a liquid crystal on the substrate.

In some embodiments, the liquid crystal or composition thereof comprises a pattern that controls cellular organization, affects the shape of the cell cultures, or both.

In various embodiments, the liquid crystal layer is placed on the substrate in a solvent-free and polymer-free matter. For example, in some embodiments, the liquid crystal layer is placed on the substrate by solvent-free and polymer-free electrospinning, solvent-free and polymer-free spin coating, solvent-free and polymer-free electrospraying, solvent-free and polymer-free airbrushing, solvent-free and polymer-free brushing, solvent-free and polymer-free 3D printing, or any combination thereof of a liquid crystal on the substrate.

In various embodiments, the liquid crystal layer is not covalently bound to the substrate. In various embodiments, the liquid crystal layer is covalently bound to the substrate.

In one embodiment, the substate is chemically inert towards the mesogenic layer. In another embodiment, the substate is reactive or interactive towards the mesogenic layer.

In various embodiments, the substrate comprises a cell tissue, organic layer, inorganic layer (e.g., metal, metal salt or metal oxide), or an organic-inorganic layer. For example, in some embodiments, the substrate is a skin, muscle, tissue layer, or any combination thereof.

In one embodiment, the substrate is a single layer substrate. In one embodiment, the substrate is a multilayer substrate. In one embodiment, the substrate comprises a uniform layer. In one embodiment, the substrate comprises a sub-layer. In some embodiment, the substrate is a stacked or side-by-side (i.e., adjacent) arrangement of substrate sublayers. In one embodiment, the substrate includes substrate sublayers that are arranged in a horizontally adjacent pattern. Thus, it should be understood that the substrate is not necessarily limited to single layers or sheets of materials. In addition, it should be understood that the surfaces of certain substrates, including the interface(s) of such substrate layers with other material(s) or layers(s), may be imperfect, wherein said surfaces represent an interpenetrating, entangled or convoluted network with other material(s) or layer(s). Similarly, it should also be understood that substrates may be uniform or discontinuous, such that the continuity of substrate layers along the length, width, and/or perimeter may be disturbed or otherwise interrupted by other layer(s) or material(s).

In one embodiment, the substrate is a rigid structure that is impermeable to liquids and gases. In this embodiment, the substrate consists of a glass plate onto which a metal, such as gold is layered by evaporative deposition. In one embodiment, the substrate is a glass plate ($SiO_2$) onto which a first metal layer, such as titanium, has been layered. A layer of a second metal, such as gold, can be then layered on top of the first metal layer.

In one embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds that are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In some embodiments, the nature of the surface of the substrate has a profound effect on the anchoring of the mesogenic layer that is associated with the surface. The surface can be engineered by the use of mechanical and/or chemical techniques. The surface of each of the above enumerated substrates can be substantially smooth. Alternatively, the surface can be roughened or patterned by rubbing, etching, grooving, stretching, stressing, impacting, nanoblasting, oblique deposition or other similar techniques known to those of skill in the art. Of particular relevance is the texture of the surface that is in contact with the mesogenic compounds.

In some embodiments, organic layers are utilized as substrate materials. In some embodiments, the organic layer is fabricated via thermal evaporation, ink-jet, organic vapor phase deposition (OVPD), organic vapor jet printing (OVJP), or any combination thereof. Other suitable fabrication methods of organic layers include spin coating and other solution-based processes. In some embodiments, the solution-based processes are carried out in nitrogen or an inert atmosphere.

In some embodiments, the substrate comprises an inorganic crystal, inorganic glass, or any combination thereof. For example, in some embodiments, the substrate is a glass, polymer, graphene, graphene oxide, graphite, metal, composite, wood, paper, rubber, fabric, fibrous network, mineral, brass, stones, natural stones used in watch dial manufacturing, laipis azul, meteorite, crystal, mineral, pearl, mother of pearl, artificial mineral (e.g., artificial sapphire), or any combination thereof. In addition, in some embodiments, the surface of the substrate is functionalized with a molecular layer, or with a polymer layer or layers, or any combination thereof.

In some embodiments, the substrate can be made of practically any physicochemically stable material. In one embodiment, the substrate material is non-reactive towards the constituents of the mesogenic layer. In some embodiments, the substrate is rigid or flexible.

In some embodiments, the substrate is optically transparent or optically opaque. In some embodiments, the substrate is an electrical insulator, conductor, semiconductor, or any combination thereof. In some embodiments, the substrate can be either permeable or impermeable to materials, such as liquids, solutions, vapors and gases. In some embodiments, the substrate is substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof.

In some embodiments, the substrate surface is prepared by rubbing, nanoblasting (i.e., abrasion of a surface with submicron particles to create roughness), or oblique deposition of a metal. In some embodiments, the substrate provides a uniform, homogenous surface, while in other embodiments, the surface is heterogenous. In some embodiments, the substrate is patterned.

In one embodiment, the substrate is glass or an organic polymer and the surface has been prepared by rubbing. Rubbing can be accomplished using virtually any material including tissues, paper, fabrics, brushes, polishing paste, etc. In one embodiment, the rubbing is accomplished by use of a diamond rubbing paste. In another embodiment, the face of the substrate that contacts the mesogenic compounds is a metal layer that has been obliquely deposited by evaporation.

In some embodiments, the substrate comprises an anisotropic surface prepared by nanoblasting a substrate with nanometer scale beads (e.g., about 1-200 nm, such as about 50-100 nm) at a defined angle of incidence (e.g., from about 5-85°, such as about 45°). The nanoblasted surface can be utilized as is or can be further modified, such as by obliquely depositing gold on the surface or by chemically functionalizing with a molecular layer so as to change its surface chemical and physical properties (Hohman J N et al., ACS Nano 2009, 3, 3, 527-536; Kim J et al., Nano Lett. 2014, 14, 5, 2946-2951; Schwartz J J et al., J. Am. Chem. Soc. 2016, 138, 18, 5957-5967).

In some embodiments, the substrate comprises an anisotropic surface prepared by stretching an appropriate substrate. For example, polymer substrates, such as polystyrene, can be stretched by heating to a temperature above the glass transition temperature of the substrate, applying a tensile force, and cooling to a temperature below the glass transition temperature before removing the force.

In some embodiments, the substrate comprises heterogenous features for use in the various devices and methods. In some embodiments, the heterogeneity is a uniform or non-uniform gradient in topography across the surface. For example, gold can be deposited onto a substrate at varying angles of incidence. Regions containing gold deposited at a near-normal angle of incidence will cause non-uniform anchoring of the liquid crystal, while areas in which the angle of incidence was greater than 10° will uniformly orient crystals. Alternatively, the heterogeneity may be the presence of two or more distinct scales topography distributed uniformly across the substrate.

In some embodiments, the substrate is patterned. The substrate can be patterned using techniques such as photolithography (Kleinfield et al., J. Neurosci. 8:4098-120 (1998)), photoetching, chemical etching, microcontact printing (Kumar et al., Langmuir 10:1498-511 (1994)), and chemical spotting.

The size and complexity of the pattern on the substrate is limited only by the resolution of the technique utilized and the purpose for which the pattern is intended. For example, using microcontact printing, features as small as 200 nm have been layered onto a substrate (e.g., Xia, Y.; Whitesides, G., J. Am. Chem. Soc. 117:3274-75 (1995)). Similarly, using photolithography, patterns with features as small as 1 &mgr;m have been produced (e.g., Hickman et al., J. Vac. Sci. Technol. 12:607-16 (1994); Smith R K et al., Progress in Surface Science, 2004, 75:1-68). Patterns which are useful in the present invention include those which comprise features such as wells, enclosures, partitions, recesses, inlets, outlets, channels, troughs, diffraction gratings and the like.

In some embodiments, the patterning is used to produce a substrate having a plurality of adjacent wells, wherein each of the wells is isolated from the other wells by a raised wall or partition and the wells do not fluidically communicate. Thus, a liquid crystal, or other substance, placed in a particular well remains substantially confined to that well. In some embodiments, the patterning allows the creation of channels through the device whereby a stimulus can enter and/or exit the device.

The pattern can be printed directly onto the substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art (e.g., Kleinfield et al., J. Neurosci. 8:4098-120 (1998); Liao W S et al., 2012, Science, 337:1517-1521). Following removal of the photoresist, a second organic layer, having a structure different from the first organic layer, can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similarly, positively or negatively charged compounds can be confined to wells having walls made of compounds with charges similar to those of the confined compounds. Similar substrate configurations are accessible through microprinting a layer with the desired characteristics directly onto the substrate (e.g., Mrkish, M.; Whitesides, G. M., Ann. Rev. Biophys. Biomol. Struct. 25:55-78 (1996); Liao W S et al, 2012, Science, 337:1517-1521).

In some embodiments, the patterned substrate controls the anchoring alignment of the liquid crystal. In one embodiment, the substrate is patterned with an organic compound (e.g., organic polymer) that forms a SAM. In one embodiment, the organic layer controls the azimuthal orientation and/or polar orientation of a supported mesogenic layer.

In addition to the ability of a substrate to anchor a mesogenic layer, an organic layer attached to the substrate is similarly able to provide such anchoring. A wide range of organic layers can be used in conjunction with the present invention. These include, but are not limited to, organic layers formed from organosulfur compounds (e.g., thiols and disulfides), organosilanes, amphiphilic molecules, cyclodextrins, polyols (e.g., poly(ethyleneglycol), poly(propylene glycol), fullerenes, and biomolecules.

An organic layer that is bound to, supported on or adsorbed onto, the surface of the substrate can anchor a mesogenic layer. As used herein, the term "anchoring" refers to the set of orientations adopted by the molecules in the mesogenic phase. The mesogenic layer will adopt particular orientations while minimizing the free energy of the interface between the organic layer and the mesogenic layer. The orientation of the mesogenic layer is referred to as an "anchoring direction." A number of anchoring directions are possible.

In some embodiments, the particular anchoring direction adopted will depend upon the nature of the mesogenic layer, the organic layer and the substrate. Anchoring directions of use in the present invention include, for example, conical anchoring, degenerate anchoring, homeotropic anchoring, multistable anchoring, planar anchoring and tilted anchoring. In some embodiments, the anchoring is a planar anchoring or homeotropic anchoring.

The anchoring of mesogenic compounds by surfaces has been extensively studied for a large number of systems (e.g., Jerome, Rep. Prog. Phys. 54:391-451 (1991)). The anchoring of a mesogenic substance by a surface is specified, in general, by the orientation of the director of the bulk phase of the mesogenic layer. The orientation of the director, relative to the surface, is described by a polar angle (measured from the normal of the surface) and an azimuthal angle (measured in the plane of the surface).

Control of the anchoring of mesogens has been largely based on the use of organic surfaces prepared by coating surface-active molecules or polymer films on inorganic (e.g., silicon oxide) substrates followed by surface treatments, such as rubbing. Other systems that have been found useful include surfaces prepared through the reactions of organosilanes with various substrates (e.g., Yang et al., In Microchemistry: Spectroscopy and Chemistry in Small Domains; Masuhara et al., Eds.; North-Holland, Amsterdam, 1994; p. 441).

Molecularly designed surfaces formed by organic layers on a substrate can be used to control both the azimuthal and polar orientations of a supported mesogenic layer. SAMs can be patterned on a surface. For example, patterned substrate or pattern organic layers made from $CH_3(CH_2)_{14}SH$ and $CH_3(CH_2)_{15}SH$ on obliquely deposited gold produce a supported mesogenic layer which is twisted 90°. Other anchoring modes are readily accessible by varying the chain length and the number of species of the organic layer constituents (e.g., Gupta and Abbott, Science 276:1533-1536 (1997)).

Transitions between anchoring modes have been obtained on a series of organic layers by varying the structure of the organic layer. The structural features which have been found to affect the anchoring of mesogenic compounds include, for example, the density of molecules within the organic layer, the size and shape of the molecules constituting the organic layer and the number of individual layers making up the bulk organic layer.

The density of the organic layer on the substrate has been shown to have an effect on the mode of mesogen anchoring. For example, transitions between homeotropic and degenerate anchorings have been obtained on surfactant monolayers by varying the density of the monolayers (e.g., Proust et al., Solid State Commun. 11:1227-30 (1972)). Thus, it is within the scope of the present invention to tailor the anchoring mode of a mesogen by controlling the density of the organic layer on the substrate.

The molecular structure, size and shape of the individual molecules making up the organic layer also affects the anchoring mode. For example, it has been demonstrated that varying the length of the aliphatic chains of surfactants on a substrate can also induce anchoring transitions; with long chains, a homeotropic anchoring is obtained while with short chains, a conical anchoring is obtained with the tilt angle O increasing as the chain becomes shorter (e.g., Porte, J. Physique 37:1245-52 (1976)). Additionally, recent reports have demonstrated that the polar angle of the mesogenic phase can be controlled by the choice of the constituents of the organic layer. e.g., Gupta and Abbott, Langmuir 12:2587-2593 (1996). The anchor can also include switchable elements, such as the photoswitchable chemical moiety azobenzene, so that the anchor can change between two or more states (e.g., Abendroth et al., ACS Nano 9:7746-7768 (2015)). The stimulation to induce switching could be light, electrochemical potential, electric field, pH, chemistry, and mechanical motion, among others. Thus, it is within the scope of the present invention to engineer the magnitude of the anchoring shift as well as the type of shift by the judicious choice of organic layer constituents.

A wide variety of organic layers are useful in practicing the present invention. These organic layers can comprise monolayers, bilayers and multilayers. Furthermore, the organic layers can be attached by covalent bonds, ionic bonds, physisorption, chemisorption and the like, including, but not limited to, hydrophobic interactions, hydrophilic interactions, van der Waals interactions and the like.

A wide variety of reaction types are available for the functionalization of a substrate surface. For example, substrates constructed of a polymer, such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliceous material, such as glass, the surface can be derivatized by reacting the surface Si—OH, SiO—H, and/or Si—Si groups with a functionalizing reagent. When the substrate is made of a metal film, the surface can be derivatized with a material displaying avidity for that metal.

Substrates can be made reactive by plasma oxidation or by other means of chemical oxidation.

The hydrophilicity of the substrate surface can be enhanced by reaction with polar molecules such as amine-, hydroxyl- and polyhydroxylcontaining molecules. Representative examples include, but are not limited to, polylysine, polyethyleneimine, poly(ethylene glycol) and poly (propylene glycol). Suitable functionalization chemistries and strategies for these compounds are known in the art (e.g., Dunn, R. L., et al., Eds. Polymeric Drugs and Drug Delivery Systems, ACS Symposium Series Vol. 469, American Chemical Society, Washington, D.C. 1991).

The hydrophobicity of the substrate surface can be modulated by using a hydrophobic spacer arm, such as, for example, long chain diamines, long chain thiols, amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer that has surfactant properties. Compounds useful for this purpose include, for example, aminated or hydroxylated detergent molecules such as, for example, 1-aminododecanoic acid.

In various embodiments, the composition further comprises a "spacer". In some embodiments, the "spacer" is a graphene, graphite, graphene oxide, boron nitride, or any combination thereof. In some embodiments, the composition comprises a "spacer" between the liquid crystal layer and at least a portion of the surface of the substrate. In some embodiments, the "spacer" acts as a glue to hold the liquid crystal layer and at least a portion of the surface of the substrate. For example, in some embodiments, the composition comprises graphene, graphite, graphene oxide, or any combination thereof that acts as a glue to hold the liquid crystal layer and at least a portion of the surface of the substrate.

In one embodiment, the liquid crystal is a liquid crystal scaffold. Thus, in one embodiment, the liquid crystal scaffold is 100% w/v liquid crystal.

In one embodiment, the composition comprises a liquid crystal scaffold. In one embodiment, the composition comprises a nonwoven liquid crystal scaffold. In one embodiment, the composition comprises an electospun nonwoven liquid crystal scaffold. For example, in one embodiment, the composition is an electrospun nonwoven cholesteryl ester liquid crystal scaffold. In some embodiments, the composition is an electrospun nonwoven cellulose-based liquid crystal scaffold.

In some embodiments, the electrospun liquid crystal scaffold has a uniform depth. In some embodiments, the electrospun liquid crystal scaffold has a non-uniform depth.

In some embodiments, the electrospun liquid crystal scaffold is functionalized, for example, by the addition of passive or active agents, such as additional therapeutic or biological agents.

In some embodiments, the electrospun liquid crystal scaffold comprises electrospun fibers. There are many factors involved in the electrospinning process, which may affect scaffolds fiber diameter and pore size. Examples of such variables include, but are not limited to, solution viscosity, surface tension, and viscoelasticity of the spinning solution. These are directly related to the concentration of, and molecular weight of the polymer, as well as the solvent used. The dielectric properties of the solution also play a key role (Kowalczyk et al., Biomacromolecules. 2008 July; 9(7):2087-90; Thompson et al., J. Polymer. 2007; 48:6913-6922; Mitchell and Sanders, J Biomed Mater Res A. 2006 July; 78(1): 1 10-20).

In some embodiments, the electrospun liquid crystal scaffold comprises a polymer. In one embodiment, the electrospun fibers comprise a polymer. For example, in one embodiment, the electrospun fibers comprise an electrospun polymer. In one embodiment, the electrospun fibers comprise an electrospun polycaprolactone or a derivative thereof.

In some embodiments, the electrospun liquid crystal scaffold comprises a polylactide or a derivative thereof. In some embodiments, the electrospun liquid crystal scaffold comprises polyurethane, preferably polyurethane based on hexamethylenediamine, polylactide derivatives, and chitosan derived material.

In some embodiments, the electrospun liquid crystal scaffold comprises a combination of synthetic polymers and naturally occurring biological material, for example a combination of collagen and PLGA. The relative amounts of the synthetic polymers and naturally occurring biological material in the matrix can be tailored to specific applications.

In one embodiment, the electrospun liquid crystal scaffolds may comprise a co-polymer. For example, in one embodiment, the electrospun fibers may comprise a co-polymer. The term "co-polymer" as used herein is intended to encompass co-polymers, ter-polymers, and higher order multiple polymer compositions formed by block, graph or random combination of polymeric components. Examples of such co-polymers include, but are not limited to poly(L-lactic-co-caprolactone), poly(ethylene glycol-co-lactide), poly(D,L-lactide-co-glycolide), poly(ethylene-co-vinyl alcohol), poly(D,L-lactic-co-glycolic acid) and PLGA-B-PEG-NH2, poly(D,L-lactic-co-glycolide), collagen and elastin, poly(L-lactic-co-caprolactone), collagen, poly(L-lactic acid), hydroxylapitate, poly(lactic-co-glycolic acid), and any combination thereof.

In some embodiments, the polymer and/or co-polymer are electrospun onto a template. In some embodiments, the template comprises a conductive collector having a pattern thereon. The collector may be formed of any electrically conductive material, such as a metal. In some embodiments, the collector is formed from aluminum, such electroplated aluminum or an aluminum sheet, such as aluminum foil or formed from an electrically conductive material comprising aluminum, brass, copper, steel, tin, nickel, titanium, silver, gold or platinum.

The pattern may be formed on the collector using any suitable method known in the art. In one embodiment, the pattern may be microfabricated on a surface of the collector. By way of example, the pattern may be microfabricated using microlithography, bonding, etching or injection molding. In one embodiment the pattern may be created by photolithography, microstereolithography or shadow masking. Preferably, the microfabricated three dimensional structures are microfabricated using microstereolithography, more preferably by a layer-by-layer photocuring approach based on the patterning of photocurable polymers, for example polyethylene glycol diacrylate.

In some embodiments, the pattern is non-conductive/insulating. Examples of non-conductive/insulating polymers, from which the pattern may be formed include example acrylated polymers, such as polyethylene glycol diacrylate, polyethylene glycol dimethacrylate or pentaerythritol tetraacrylate. Alternatively, the pattern may be formed from thiol-ene based polymers, or ceramics, such as ORMOCER.

In some embodiments, the pattern is dimensioned to provide a scaffold comprising at least one cavity capable of acting as a stem cell niche. Preferably, the pattern provides a scaffold having a cavity having a diameter of from 10 μm to 500 μm, preferably from 50 μm to 400 μm, still more preferably from 150 μm to 300 μm and a depth of from 10 μm to 1000 μm, preferably a depth of from 50 μm to 150 μm.

In some embodiments, the pattern is dimensioned to provide a scaffold of nonuniform depth.

In some embodiments, the pattern is dimensioned to provide a scaffold comprising multiple cavities.

In some embodiments, the electrospun liquid crystal scaffold comprises at least one cavity. For example, in some embodiments, the electrospun liquid crystal scaffold comprises at least one cavity therein capable of acting as a stem cell niche. In some embodiments, the electrospun liquid crystal scaffold comprises an edible polymer or co-polymer, wherein said scaffold comprises at least one cavity therein capable of acting as a stem cell niche.

In some embodiments, the cavity has a diameter of from 10 μm to 500 μm, preferably from 50 μm to 400 μm, still more preferably from 150 μm to 300 μm and a depth of from 10 μm to 1000 μm, preferably from 50 μm to 150 μm. Preferably, the scaffold comprises multiple cavities, for example at least 5, 10 15, 20, 50, 100, 200 or 500 cavities.

Thus, in some embodiments, the cavity comprises at least one cell. Examples of such cell include, but are not limited to a tissue cell, epithelial cell, endothelial cell, muscle cell, neuron, adipocyte, cardiac cell, stem cell (e.g., a muscle stem cell, mesenchymal stem cell, epithelial stem cell, etc.), hematopoietic stem cell, bone marrow cell, gland cell, mammary gland cell, human mammary gland cell, epidermal cell, keratinocyte, lactocytes, hepatic cell, beta cells pancreatic cell, C2C12 myoblast, iPSC, MSC, iPSC muscle progenitor, or any combination thereof.

The aforementioned cells may be seeded into the cavity by any technique known in the art. For example, in some embodiments, the cells may be electrosprayed into the cavity, pipetted into the cavity, flowed into the cavity via a bioreactor, or any combination thereof.

In various aspects of the present invention, the composition may further comprise at least one cell that promotes maintenance of the stem cell, for example, a specialized support cell for the muscle cell, such as fibroblasts.

In some embodiments, the composition may further comprise any extracellular matrix component, such as fibronectin, vitronectin, collagen, laminin.

In some embodiments, the composition may further comprise naturally occurring materials. Examples of suitable naturally occurring materials include, but are not limited to, amino acids, polypeptides, denatured peptides such as gelatin from denatured collagen, carbohydrates, lipids, nucleic acids, glycoproteins, lipoproteins, glycolipids, glycosaminoglycans, and proteoglycans. In one embodiment the naturally occurring material is an extracellular matrix material, for example collagen, fibrin, elastin, laminin, fibronectin, heparin, fibrinogen. Such extracellular matrix material may be isolated from cells, such as mammalian cells, for example of human origin. Preferably the naturally occurring material is collagen. Alternatively, the naturally occurring polymer is chitin. Preferably the scaffold is biodegradable, i.e., is formed of biodegradable materials, such as biodegradable polymers naturally occurring biological material. Examples of suitable biodegradable materials include, but are not limited to collagen, poly(alpha esters) such as poly(lactate acid), poly(glycolic acid), polyorthoesters, polyanhydrides polyglycolic acid and polyglactin, and copolymers thereof.

For example, in some embodiments, the properties of the electrospun liquid crystal scaffolds can be adjusted in accordance with the needs and specifications of the cells to be suspended and grown within them. The porosity, for instance, can be varied in accordance with the method of making the electrospun materials matrix. As used herein, a natural biological polymer material can be a naturally occurring organic material including any material naturally found in the body of a mammal, plant, or other organism.

In some embodiments, the method comprises culturing of the at least one cell of interest for at least 1 hr. In some embodiments, the method comprises culturing of the at least one cell of interest for at least 2 hr. In some embodiments, the method comprises culturing of the at least one cell of interest for at least 3 hr. In some embodiments, the method comprises culturing of the at least one cell of interest for at least 4 hr. In some embodiments, the method comprises culturing of the at least one cell of interest for at least 5 hr. In some embodiments, the method comprises culturing of the at least one cell of interest for at least 6 hr. In some embodiments, the method comprises culturing of the at least one cell of interest for at least 7 hr. In some embodiments, the method comprises culturing of the at least one cell of interest for at least 8 hr. In some embodiments, the method comprises culturing of the at least one cell of interest for at least 9 hr. In some embodiments, the method comprises culturing of the at least one cell of interest for at least 10 hr. In some embodiments, the method comprises culturing of the at least one cell of interest for at least 11 hr. In some embodiments, the method comprises culturing of the at least one cell of interest for at least 12 hr. In some embodiments, the method comprises culturing of the at least one cell of interest for at least 14 hr. In some embodiments, the method comprises culturing of the at least one cell of interest for at least 15 hr. In some embodiments, the method comprises culturing of the at least one cell of interest for at least 24 hr. In some embodiments, the method comprises culturing of the at least one cell of interest for at least 48 hr. In some embodiments, the method comprises culturing of the at least one cell of interest for at least 72 hr. In some embodiments, the method comprises culturing of the at least one cell of interest for at least 2 weeks (e.g., for muscle differentiation).

In some embodiments, the method comprises culturing of the at least one cell of interest indefinitely (e.g., for cancer cell growth). In some embodiments, the method comprises culturing of the at least one cell of interest until cell culture media and nutrients are removed from cultured environments.

In various embodiments, the method comprises a stimulus. In various embodiments, the stimulus induces cell growth, cell-culturing, generating at least one cell tissue layer, organoid, spheroid, 3D cell aggregate, or any combination thereof. In one embodiment, the stimulus is any stimulus described herein. For example, in some embodiments, the stimulus is selected from the group consisting of a light stimulus, electrical stimulus, and mechanical stimulus.

For example, in one embodiment, the method comprises thermal stimulus. For example, in some embodiments, the temperature of between about 15° C. to about 40° C. promotes the formation of liquid crystal striations inducing cell growth, cell-culturing, generating at least one cell tissue layer, organoid, spheroid, 3D cell aggregate, and any combination thereof. In some embodiments, the temperature of between about 20° C. to about 40° C. promotes the formation of liquid crystal striations inducing cell growth, cell-culturing, generating at least one cell tissue layer, organoid, spheroid, 3D cell aggregate, and any combination thereof. In some embodiments, the temperature of between about 32° C. to about 40° C. promotes the formation of liquid crystal striations inducing cell growth, cell-culturing, generating at least one cell tissue layer, organoid, spheroid, 3D cell aggregate, and any combination thereof. In some embodiments, the temperature of between about 34° C. to about 38° C. promotes the formation of liquid crystal striations inducing cell growth, cell-culturing, generating at least one cell tissue layer, organoid, spheroid, 3D cell aggregate, and any combination thereof. In some embodiments, the temperature of between about 30° C. to about 32° C. promotes the formation of liquid crystal striations inducing cell growth, cell-culturing, generating at least one cell tissue layer, organoid, spheroid, 3D cell aggregate, and any combination thereof. In some embodiments, the temperature of between about 27° C. to about 29° C. promotes the formation of liquid crystal striations inducing cell growth, cell-culturing, generating at least one cell tissue layer, organoid, spheroid, 3D cell aggregate, and any combination thereof. In some embodiments, the temperature of between about 23° C. to about 27° C. promotes the formation of liquid crystal striations inducing cell growth, cell-culturing, generating at least one cell tissue layer, organoid, spheroid, 3D cell aggregate, and any combination thereof. In some embodiments, the temperature of between about 23° C. to about 25° C. promotes the formation of liquid crystal striations inducing cell growth, cell-culturing, generating at least one cell tissue layer, organoid, spheroid, 3D cell aggregate, and any combination thereof. In some embodiments, the temperature of between about 15° C. to about 23° C. promotes the formation of liquid crystal striations inducing cell growth, cell-culturing, generating at least one cell tissue layer, organoid, spheroid, 3D cell aggregate, and any combination thereof (e.g., for fish cells, cold water fish cells, or invertebrate cells). In some embodiments, the temperature of between about 15° C. to about 20° C. promotes the formation of liquid crystal striations inducing cell growth, cell-culturing, generating at least one cell tissue layer, organoid, spheroid, 3D cell aggregate, and any combination thereof.

In some embodiments, the method comprises the steps of inducing a phase change of the liquid crystal or composition thereof and inducing cellular aggregation of at least one cell of interest (e.g., anchorage-dependent cell).

In some embodiments, the method further comprises the steps of dissociating the liquid crystal and detaching the cultured cells. In some embodiments, the step of detaching the cultured cells comprises any detaching method known in the art. For example, in some embodiments, the step of detaching the cultured cells comprises at least one of enzymatic treatment, mechanical force, fluid shear force, acoustic waves, self-migration of the cells by tilting, and self-migration of the cells by chemical signals.

In some embodiments, the method further comprises the step of coating a surface of a substrate with the liquid crystal or composition thereof.

In some embodiments, the substrate comprises any substrate described herein. For example, in some embodiments, the substrate is a multi-well plate for multiplexed bioassays.

In one aspect, the present invention provides a method of inducing and/or propagating cellular agriculture of at least one cell or cell tissue layer of interest (e.g., human organ, cancer cell models, cancer spheroids for drug testing, anchorage-dependent cell, etc.). For example, in one embodiment, the method induces and/or propagates organ cell tissue layer of interest. Thus, in one aspect, the present invention provides a method of generating organoids mimicking organs and/or multiple organs.

In one aspect, the present invention also provides a method of coating a surface of a substrate, wherein the method comprises coating the surface of the substrate with an organoid or spheroid. In some embodiments, the method comprises continuous organoid formation or spheroid formation.

In some embodiments, the organoid or spheroid self-assemble into aggregates. In some embodiments, the organoid is manufactured using the method of the present invention. In some embodiments, the spheroid is manufactured using the method of the present invention.

In some embodiments, the surface of the substrate is a slanted surface. In some embodiments, the surface of the substrate is a flat surface for a period of time followed by tilting of the surface for harvesting of the cells. In some embodiments, the substrate is a multi-well plate for multiplex bioassays.

In another aspect, the present invention provides a method of manufacturing an organoid, wherein the method comprises culturing stem cells (e.g., anchorage-dependent stem cell) in the presence of a liquid crystal or a composition thereof. In some embodiments, the method comprises evaluating the development of the stem cells toward different lineages.

In one aspect, the present invention also provides a method of harvesting cultured cells. In some embodiments, the method comprises dissociating the liquid crystal; and detaching the cultured cells. In some embodiments, the method comprises detaching the cultured cells by enzymatic treatment, mechanical force, fluid shear force, acoustic waves, self-migration of the cells by tilting, self-migration of the cells by chemical signals, or any combination thereof.

In some embodiments, the step of culturing cells (e.g., anchorage-dependent cells) is performed in an oxygen-containing environment. In some embodiments, the step of culturing cells is performed in an oxygen-free environment.

Devices

The present invention also provides a cell culturing device comprising a first surface area. In some embodiments, at least a portion of the first surface area is coated with a first liquid crystal or a composition thereof.

In some embodiments, the cell culturing device comprises at least one well having a bottom surface and a sidewall. In some embodiments, the first surface area is the bottom surface of the at least one well.

In some embodiments, the cell culturing device comprises a plurality of wells.

In some embodiments, the cell culturing device comprises a high-temperature resistant material. In some embodiments, the cell culturing device comprises a biocompatible material. In some embodiments, the cell culturing device comprises an optically transparent biocompatible material. Examples of such material include, but are not limited to, polystyrene, polycarbonate, polydimethylsiloxane (PDMS), polymethylmethacrylate (PMMA), glass, quartz, or any combination thereof. For example, in some embodiments, the cell culturing device comprises an optically transparent biocompatible material allowing for real-time visual monitoring.

In some embodiments, the cell culturing device comprises any device known in the art that can grow, support, and/or maintain cells. In some embodiments, the device can grow, support, and/or maintain cells on the surface of the device, inside the device, or both. Examples of such device include, but are not limited to, a chip, slide, microscope slide, cell culture plate, cell culture dish, petri dish, cell culture flask, multi-well plate, cell culturing vessel, channel array, microfluidic channel array, biological cabinet, incubator, or any combination thereof. Thus, for example, in some embodiments, the cell culturing device comprises a multi-well plate. In some embodiments, the cell culturing device comprises a multi-well plate comprising at least one well having a bottom surface and a sidewall, wherein the first surface area is the bottom surface of the at least one well.

In some embodiments, the geometry of the well facilitates even distribution of nutrients and/or gases. In some embodiments, the geometry of the well minimizes the formation of gradients.

In some embodiments, at least a portion of the first surface area is exposed to an oxygen-containing environment. In some embodiments, at least a portion of the first surface area is exposed to an oxygen-free environment.

In some embodiments, at least a portion of the first surface area comprises a planar surface. In some embodiments, at least a portion of the first surface area comprises a patterned surface. For example, in some embodiments, at least a portion of the first surface area comprises a patterned surface with micro- and/or nano-scale topographies to promote cell adhesion and/or cell alignment of the cell of interest (e.g., anchorage-dependent cell).

In some embodiments, at least a portion of the first surface area comprises a gas impermeable material. In some embodiments, at least a portion of the first surface area comprises a gas permeable material.

In some embodiments, the gas permeable material has permeability to oxygen at a permeability coefficient of at least about 100 [$cm^3$][cm]/[$cm^2$][s][cm Hg]. In some embodiments, the gas permeable material has permeability to oxygen at a permeability coefficient of at least about 350 [$cm^3$][cm]/[$cm^2$][s][cm Hg]. In some embodiments, the gas permeable material has permeability to oxygen at a permeability coefficient of at least about 1000 [$cm^3$][cm]/[$cm^2$][s][cm Hg]. In some embodiments, the gas permeable material has permeability to oxygen at a permeability coefficient of at least about 2000 [$cm^3$][cm]/[$cm^2$][s][cm Hg].

In some embodiments, the gas permeable material has permeability to carbon dioxide at a permeability coefficient of at least about 100 [$cm^3$][cm]/[$cm^2$][s][cm Hg]. In some embodiments, the gas permeable material has permeability to carbon dioxide at a permeability coefficient of at least about 350 [$cm^3$][cm]/[$cm^2$][s][cm Hg]. In some embodiments, the gas permeable material has permeability to carbon dioxide at a permeability coefficient of at least about 1000 [$cm^3$][cm]/[$cm^2$][s][cm Hg]. In some embodiments, the gas permeable material has permeability to carbon dioxide at a permeability coefficient of at least about 2000 [$cm^3$][cm]/[$cm^2$][s][cm Hg].

In some embodiments, the gas permeable material is any gas permeable material known in the art. Example of such gas permeable material include, but are not limited to, a silicone-containing material, such as poly(dimethyl siloxane) (PDMS) and polymethylpentene.

In some embodiments, the first liquid crystal is not covalently bound to the first surface area of the device. In some embodiments, the first liquid crystal is covalently bound to the first surface area of the device.

In some embodiments, the first liquid crystal comprises any liquid crystal described herein.

For example, in some embodiments, the first liquid crystal or composition thereof comprises at least one selected from the group consisting of cholesteryl oleyl carbonate or a derivative thereof, cholesteryl pelargonate or a derivative thereof, and cholesteryl benzoate or a derivative thereof. In some embodiments, the first liquid crystal is a cholesteryl ester liquid crystal.

In some embodiments, the first liquid crystal or composition thereof comprises a pattern that controls cellular organization, affects the shape of cell cultures, or both.

In some embodiments, the first liquid crystal or composition thereof displays a phase change between about 10° C. and about 60° C. For example, in some embodiments, the first liquid crystal or composition thereof displays a phase change between about 32° C. and about 42° C. In some embodiments, the first liquid crystal or composition thereof displays a phase change at about 37° C. to induce cellular aggregation of anchorage-dependent cells. In some embodiments, the first liquid crystal or composition thereof displays a phase change at about 37° C. induced by helical aggregation, which then induces cellular aggregation of cultured anchorage-dependent cells (e.g., anchorage-dependent eukaryotic cells).

In some embodiments, the composition comprises any composition described herein.

For example, in some embodiments, the composition comprises at least one component selected from the group consisting of a composite, a substrate, a cholesteryl ester liquid crystal-based scaffold, and an additive. In some embodiments, the component in the composition is not covalently bound to the first liquid crystal. In some embodiments, the component in the composition is covalently bound to the first liquid crystal.

In some embodiments, the device comprises a second surface area. In some embodiments, at least a portion of the second surface area is coated with a second liquid crystal or a composition thereof that is different from the first liquid crystal or composition thereof.

In some embodiments, at least a portion of the second surface area is exposed to an oxygen-containing environment. In some embodiments, at least a portion of the second surface area is exposed to an oxygen-free environment.

In some embodiments, at least a portion of the second surface area comprises a planar surface. In some embodiments, at least a portion of the second surface area comprises a patterned surface. For example, in some embodiments, at least a portion of the second surface area comprises a patterned surface with micro- and/or nano-scale topographies to promote cell adhesion and/or cell alignment of the cell of interest (e.g., anchorage-dependent cell).

In some embodiments, at least a portion of the second surface area comprises a gas impermeable material. In some embodiments, at least a portion of the second surface area comprises a gas permeable material.

In some embodiments, the gas permeable material is any gas permeable material described herein. For example, in some embodiments, the gas permeable material has permeability to oxygen at a permeability coefficient of at least about 350 [$cm^3$][cm]/[$cm^2$][s][cm Hg] and permeability to carbon dioxide at a permeability coefficient of at least about 2000 [$cm^3$][cm]/[$cm^2$][s][cm Hg].

In some embodiments, the second liquid crystal is not covalently bound to the second surface area of the device. In some embodiments, the second liquid crystal is covalently bound to the second surface area of the device.

In some embodiments, the second liquid crystal comprises any liquid crystal described herein.

In some embodiments, the cell culturing device further comprises a heating element. In some embodiments, the cell culturing device comprises a heater for controlling the temperature of the cell culture reservoir. In such a configuration, the cell culturing device can operate autonomously without an incubator, with only a source of electrical power. In some embodiments, the cell culturing device comprises a heater for localized temperature control.

In some embodiments, the cell culturing device further comprises one or more sensors operably coupled to the cell culture device. In some embodiments, the cell culturing device further comprises one or more sensors operably coupled to the at least one well. The sensors may be capable of measuring one or more parameters within the cell culture device, such as pH, dissolved oxygen, total biomass, cell diameter, glucose concentration, lactate concentration, cell metabolite concentration, etc. In some embodiments, the one or more sensors are operably coupled to a computer system having a central processing unit for carrying out instructions, such that automatic monitoring and adjustment of parameters is possible.

In some embodiments, the cell culturing device further comprises at least one component that regulates temperature, pH, gas exchange, and/or humidity. For example, in some embodiments, the cell culturing device comprises a gas-permeable membrane that allows for oxygen and/or carbon dioxide diffusion while maintaining sterility. In some embodiments, the cell culturing device comprises a sensor monitoring pH and/or dissolved oxygen.

In some embodiments, the cell culturing device may be configured as a modular system, with interchangeable components for ease of cleaning, sterilization, and/or customization.

Methods of Evaluating Cancer Treatment

The present invention also provides a method of evaluating a cancer treatment.

In some embodiments, the method comprises manufacturing at least one 3D cell aggregate using the method of the present invention; applying the cancer treatment to the 3D cell aggregate; measuring a variable of the 3D cell aggregate; and determining the cancer treatment is effective when the variable of the 3D cell aggregate decreased when compared to a comparator.

In some embodiments, the variable of the 3D cell aggregate comprises at least one selected from the group consisting of a size of the 3D cell aggregate, viability of the 3D cell aggregate, metabolic activity of the 3D cell aggregate, cellular behavior of the 3D cell aggregate, proteomics of the 3D cell aggregate, lipidomics of the 3D cell aggregate, and transcriptomics of the 3D cell aggregate.

In various embodiments of the methods of the invention, the variable of the 3D cell aggregate is determined to be decreased when the variable of the 3D cell aggregate is decreased by at least 0.1%, by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared to a comparator.

In various embodiments of the methods of the invention, the variable of the 3D cell aggregate is determined to be decreased when the variable of the 3D cell aggregate is decreased by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In various embodiments, the comparator is the variable of the 3D cell aggregate before applying a cancer treatment. In one embodiment, the comparator is the variable of the 3D cell aggregate that did not receive a cancer treatment. In another embodiment, the comparator is the variable of the 3D cell aggregate that receive a non-cancer treatment. In another embodiment, the comparator is the variable of the 3D cell aggregate that receive a different cancer treatment.

In some embodiments, the method comprises manufacturing at least one 3D cell aggregate using the method of the present invention; applying the cancer treatment to the 3D cell aggregate; measuring a variable of the 3D cell aggregate; and determining the cancer treatment is effective when the variable of the 3D cell aggregate decreased when compared to a comparator.

In some embodiments, the variable of the tumor organoids comprises at least one selected from a size of the tumor organoid, viability of the tumor organoid, metabolic activity of the tumor organoid, cellular behavior of the tumor organoid, proteomics of the tumor organoid, lipidomics of the tumor organoid, or transcriptomics of the tumor organoid.

In various embodiments of the methods of the invention, the variable of the tumor organoid is determined to be decreased when the variable of the tumor organoid is decreased by at least 0.1%, by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared to a comparator.

In various embodiments of the methods of the invention, the variable of the tumor organoid is determined to be decreased when the variable of the tumor organoid is decreased by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In various embodiments, the comparator is the variable of the tumor organoid before applying a cancer treatment. In one embodiment, the comparator is the variable of a tumor organoid that did not receive a cancer treatment. In another embodiment, the comparator is the variable of a tumor organoid that receive a non-cancer treatment. In another embodiment, the comparator is the variable of a tumor organoid that receive a different cancer treatment.

In another aspect, the present invention provides a method of evaluating a cancer treatment, wherein the method comprises manufacturing at least one tumor spheroid using the method of the present invention; applying the cancer treatment to the tumor spheroid; measuring a variable of the tumor spheroid; and determining the cancer treatment is effective when the variable of the tumor spheroid decreased when compared to a comparator.

In some embodiments, the variable of the tumor spheroid comprises at least one selected from a size of the tumor spheroid, viability of the tumor spheroid, metabolic activity of the tumor spheroid, cellular behavior of the tumor spheroid, proteomics of the tumor spheroid, lipidomics of the tumor spheroid, or transcriptomics of the tumor spheroid.

In various embodiments of the methods of the invention, the variable of the tumor spheroid is determined to be decreased when the variable of the tumor spheroid is decreased by at least 0.1%, by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared to a comparator.

In various embodiments of the methods of the invention, the variable of the tumor spheroid is determined to be decreased when the variable of the tumor spheroid is decreased by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In various embodiments, the comparator is the variable of the tumor spheroid before applying a cancer treatment. In one embodiment, the comparator is the variable of a tumor spheroid that did not receive a cancer treatment. In another embodiment, the comparator is the variable of a tumor spheroid that receive a non-cancer treatment. In another embodiment, the comparator is the variable of a tumor spheroid that receive a different cancer treatment.

Methods of Preparation

The present invention also relates, in part, to methods, techniques, and strategies for fabricating and characterizing the liquid crystals or compositions or cell culturing devices thereof described herein. In one aspect, the present invention relates, in part, to methods of generating the liquid crystal described herein. In another aspect, the present invention relates, in part, to methods generating the liquid crystal scaffold described herein. In another aspect, the present invention relates, in part, to methods generating the cell culturing device described herein.

In some embodiments, the method is a solvent-free method, polymer-free method, or a combination thereof.

For example, in one embodiment, the method of generating a liquid crystal (e.g., liquid crystal scaffold comprising 100% w/v liquid crystal) comprise generating a liquid crystal mesogen comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof; melting the liquid crystal mesogen; and cooling the liquid crystal mesogen to generate a viscous liquid.

In various embodiments, the liquid crystal mesogen can be generated using any method described herein.

In some embodiments, the liquid crystal composition can be generated using any method described herein. In one embodiment, the method of generating a liquid crystal composition (e.g., a liquid crystal scaffold) comprise generating a liquid crystal mesogen comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof; melting the liquid crystal mesogen; cooling the liquid crystal mesogen to generate a viscous liquid; and placing the viscous liquid on at least a portion of a surface of a first substrate to generate the liquid crystal scaffold. For example, in some embodiments, the liquid crystal scaffold can be generated by melting the liquid crystal mesogen at about 60° C.; cooling the liquid crystal mesogen to generate a viscous liquid; and placing the viscous liquid on at least a portion of the internal surface of the substrate.

In some embodiments, the viscous liquid can be placed on at least a portion of the internal surface of the substrate using any method described herein. For example, in one embodiment, the viscous liquid can be placed on at least a portion of the internal surface of the substrate using solvent-free electrospinning, solvent-free spin coating, solvent-free electrospraying, solvent-free airbrushing, solvent-free brushing, or any combination thereof.

In various embodiments, the substrate can be prepared using any method described herein. For example, in some embodiments, the substrate surface is prepared by rubbing, nanoblasting (i.e., abrasion of a surface with submicron particles to create roughness), or oblique deposition of a metal. In some embodiments, the substrate provides a uniform, homogenous surface, while in other embodiments, the surface is heterogenous. In some embodiments, the substrate is patterned.

In some embodiments, the method of generating cell culturing device comprises generating a liquid crystal mesogen comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof; melting the liquid crystal mesogen; cooling the liquid crystal mesogen to generate a viscous liquid; and placing the viscous liquid on at least a portion of a first surface to generate the liquid crystal scaffold. For example, in some embodiments, the liquid crystal scaffold can be generated by melting the liquid crystal mesogen at about 60° C.; cooling the liquid crystal mesogen to generate a viscous liquid; and placing the viscous liquid on at least a portion of the first surface.

In some embodiments, the viscous liquid can be placed on at least a portion of the first surface using any method described herein. For example, in one embodiment, the viscous liquid can be placed on at least a portion of the first surface using solvent-free electrospinning, solvent-free spin coating, solvent-free electrospraying, solvent-free airbrushing, solvent-free brushing, or any combination thereof.

In various embodiments, the surface can be prepared using any method described herein. For example, in some embodiments, the surface is prepared by rubbing, nanoblasting (i.e., abrasion of a surface with submicron particles to create roughness), or oblique deposition of a metal. In some embodiments, the surface provides a uniform, homogenous surface, while in other embodiments, the surface is heterogenous. In some embodiments, the surface is patterned.

In one embodiment, the method comprises a polymer. In one embodiment, the method of generating a liquid crystal composition (e.g., a liquid crystal scaffold) comprise generating a liquid crystal mesogen comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof; melting the liquid crystal mesogen; cooling the liquid crystal mesogen to generate a viscous liquid; and mixing the viscous liquid with at least one polymer to generate the liquid crystal scaffold.

In other embodiments, the present invention provides a method for producing an electrospun scaffold, comprising electrospinning a polymer or co-polymer onto a template comprising a conductive collector having a three-dimensional pattern thereon, wherein said electrospun polymer or copolymer preferentially deposits onto said three-dimensional pattern.

In other embodiments, the method comprises a solvent. In some embodiments, the solvent serves as a medium for a reaction that generates a liquid crystal mesogen comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof. In some embodiments, the solvent serves as a medium for a medium for the distribution of components of different phases or extraction of components into said solvent. For example, in one embodiment, the solvent serves as a medium for a medium for the distribution of the viscous liquid crystals liquid while placing the viscous liquid on at least a portion of a surface of a first substrate to generate the liquid crystal layer on the substrate.

For example, in one embodiment, the method of generating a liquid crystal composition (e.g., a liquid crystal scaffold) comprise generating a liquid crystal mesogen comprising cholesteryl oleyl carbonate or a derivative or a salt thereof, cholesteryl pelargonate or a derivative or a salt thereof, cholesteryl benzoate or a derivative or a salt thereof, cellulose or a derivative or a salt thereof, or any combination thereof; melting the liquid crystal mesogen; cooling the liquid crystal mesogen to generate a viscous liquid; dispersing the viscous liquid and at least one polymer in a solvent; and electrospinning the liquid crystal and the at least one polymer to generate the liquid crystal scaffold.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: A Dynamic Cholesteric Liquid Crystal for Organoid, Spheroid, and 3D Cell Aggregate Manufacturing The present studies provide a scaffold to generate rapid three-dimensional cellular aggregates using a biocompatible cholesteric liquid crystal (CLC) biomaterial. The CLC material was applied as a film, and cells were seeded on the film's surface within short cell culture periods of less than 5 hr large cellular aggregates were generated and grow over time. Multiple cell types have been tested and work with this technology and the mechanical stimulation provided by the phase transition engineered in the CLC biomaterial, a temperature relevant to the cell culture incubator.

Example 2: Generation of CLC Substrates

Varying ratio of mesogen were weighted to generate a scaffold with desirable phase transition. The mesogens were heated to the melt phase of about 80° C. and then pipetted onto surfaces to create CLC-coated substrates. The substrates were then placed in well plates cell culture media and cells were added to the substrates using traditional cell seeding techniques. The scaffold directed cellular organization once the scaffold was placed in the cell culture incubator with seeded cells on the surface.

Example 3: Method for Cell Culture on CLC

All the chemicals were purchased from Sigma Aldrich, while cell culture reagents were purchased from Fisher Scientific. Cells were obtained from ATCC. Cholesteryl oleyl carbonate, cholesteryl pelargonate, and cholesteryl benzoate were mixed at a ratio to produce CLC with various mesophase temperatures (Tm). CLC was heated to 100° C. to create a clear homogeneous solution and patterned with a 60 μm thickness using a screen-printing method on glass-bottom well plates. CLC coated well; plated were UV sterilized for 1 hour.

C2C12 cells were stained with Cell Tracker Green according to the product protocol (thermofisher.com/document-connect/document-connect.html?url=https%3A%2F%2Fassets.thermofisher.com%2FTFS-Assets%2FLSG%2Fmanuals%2FMAN0001826_CellTracker_Probes_PI.pdf). To explain briefly, the culture medium was removed and cells were washed with PBS. Then cells were incubated with a basal medium containing CellTracker Geen at the final concentration of 10 uM for 45 min. After staining, cells were detached by adding Trypsin 0.25%. Cells were again resuspended in a complete culture medium at the desired concentration and directly seeded on CLC-coated wells. Cells were monitored continuously over 24 hr using an inverted microscope equipped with a cell culture incubator. The size distribution and movement of the cells were analyzed with ImageJ post-experiments.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of co-culturing at least one anchorage-dependent cell with at least one second cell, wherein the method comprises:

coating a surface of a cell culture plate with a liquid crystal or composition thereof;

co-culturing the at least one anchorage-dependent cell and the at least one second cell in the presence of the liquid crystal or a composition thereof; and inducing a phase change of the liquid crystal or composition thereof, thereby inducing cellular aggregation of the at least one anchorage-dependent cell and the at least one second cell.

2. The method of claim 1, wherein the cell culturing plate is a multi-well plate for multiplexed bioassays.

3. The method of claim 1, wherein the at least one anchorage-dependent cell is at least one selected from the group consisting of a cancer cell, an epithelial cell, an endothelial cell, a fibroblast, a muscle cell, a myoblast cell, a neuron, an adipocyte, a cardiac cell, a hematopoietic a stem cell, a bone marrow cell, a gland cell, a mammary gland cell, a human mammary gland cell, an epidermal cell, a keratinocyte, a lactocyte, a hepatic cell, a pancreatic beta cell, a human cell, a mammalian cell, a vertebrate cell, an invertebrate cell, a bacterial cell, a human dermal fibroblast, a human keratinocyte, a human epidermal cell, a human cancer cell, a human brain cancer cell, a bovine satellite cell, a C2C12 myoblast, an induced pluripotent stem cell (iPSC), a mesenchymal stem cell (MSC), and an iPSC muscle progenitor.

4. The method of claim 1, wherein the liquid crystal or composition thereof comprises at least one selected from the group consisting of cholesteryl oleyl carbonate, cholesteryl pelargonate, and cholesteryl benzoate.

5. The method of claim 1, wherein the liquid crystal is a cholesteryl ester liquid crystal.

6. The method of claim 1, wherein the liquid crystal or composition thereof comprises a pattern that controls cellular organization.

7. The method of claim 1, wherein the composition comprises at least one selected from the group consisting of a composite, a substrate, and an additive.

8. The method of claim 1, wherein the liquid crystal or composition thereof displays a phase change between about 17° C. and about 42° C.

9. The method of claim 1, further comprising the steps of dissociating the liquid crystal and detaching the liquid crystal from the cultured cells.

10. The method of claim 9, wherein the step of detaching the liquid crystal comprises at least one of enzymatic treatment, mechanical force, fluid shear force, acoustic waves, self-migration of the cells by tilting, and self-migration of the cells by chemical signals.

11. The method of claim 1, wherein the composition comprises at least one component selected from the group consisting of a composite, a substrate, a cholesteryl ester liquid crystal-based scaffold, and an additive, wherein the at least one component is not covalently bound to the liquid crystal.

12. The method of claim 1, wherein the at least one anchorage-dependent cell and the at least one second cell form a 3D cell aggregate.

13. The method of claim 12, wherein the method produces a 3D cell aggregate comprises at least one selected from the group consisting of a spheroid, a tumor spheroid, a stem cell spheroid, an organoid, a tumor organoid, a meat organoid, a fish organoid, an insulin generating organoid, a milk generating organoid, a blood generating organoid, a blood cell organoid, a blood product generating organoid, an extracellular matrix organoid, and a stem cell organoid.

14. The method of claim 12, wherein the at least one anchorage-dependent cell is at least one selected from the group consisting of a cancer cell, an epithelial cell, an endothelial cell, a fibroblast, a muscle cell, a myoblast cell, a neuron, an adipocyte, a cardiac cell, a hematopoietic a stem cell, a bone marrow cell, a gland cell, a mammary gland cell, a human mammary gland cell, an epidermal cell, a keratinocyte, a lactocyte, a hepatic cell, a pancreatic beta cell, a human cell, a mammalian cell, a vertebrate cell, an invertebrate cell, a bacterial cell, a human dermal fibroblast, a human keratinocyte, a human epidermal cell, a human cancer cell, a human brain cancer cell, a bovine satellite cell, a C2C12 myoblast, an induced pluripotent stem cell (iPSC), a mesenchymal stem cell (MSC), and an iPSC muscle progenitor.

15. The method of claim 12, wherein the liquid crystal or composition thereof comprises at least one selected from the group consisting of cholesteryl oleyl carbonate, cholesteryl pelargonate, and cholesteryl benzoate.

16. The method of claim 12, wherein the liquid crystal is a cholesteryl ester liquid crystal.

17. The method of claim 12, wherein the composition comprises at least one selected from the group consisting of a composite, a substrate, and an additive.

18. The method of claim 12, further comprising the steps of dissociating the liquid crystal and detaching the liquid crystal from the cultured cells.

19. The method of claim 18, wherein the step of detaching the liquid crystal comprises at least one of enzymatic treatment, mechanical force, fluid shear force, acoustic waves, self-migration of the cells by tilting, and self-migration of the cells by chemical signals.

* * * * *